US012378196B2

(12) United States Patent
Simon et al.

(10) Patent No.: US 12,378,196 B2
(45) Date of Patent: Aug. 5, 2025

(54) SYNTHESIS OF (S)-6-HYDROXYTRYPTOPHAN AND DERIVATIVES THEREOF

(71) Applicant: Heidelberg Pharma Research GmbH, Ladenburg (DE)

(72) Inventors: Werner Simon, Ladenburg (DE); Susanne Werner-Simon, Ladenburg (DE); Christoph Müller, Ladenburg (DE)

(73) Assignee: Heidelberg Pharma Research GmbH, Ladenburg (DE)

( * ) Notice: Subject to any disclaimer, the term of this patent is extended or adjusted under 35 U.S.C. 154(b) by 948 days.

(21) Appl. No.: 17/312,308

(22) PCT Filed: Dec. 11, 2019

(86) PCT No.: PCT/EP2019/084544

§ 371 (c)(1),
(2) Date: Jun. 9, 2021

(87) PCT Pub. No.: WO2020/120525

PCT Pub. Date: Jun. 18, 2020

(65) Prior Publication Data

US 2022/0024870 A1 Jan. 27, 2022

(30) Foreign Application Priority Data

Dec. 11, 2018 (EP) .................................... 18211747

(51) Int. Cl.

| | |
|---|---|
| ***C07D 209/20*** | (2006.01) |
| ***A61K 47/64*** | (2017.01) |
| ***B01J 31/22*** | (2006.01) |
| ***B01J 31/24*** | (2006.01) |
| ***C07K 7/64*** | (2006.01) |

(52) U.S. Cl.

CPC ............ *C07D 209/20* (2013.01); *A61K 47/64* (2017.08); *B01J 31/2295* (2013.01); *B01J 31/2409* (2013.01); *C07K 7/64* (2013.01); *B01J 2231/645* (2013.01); *B01J 2531/822* (2013.01)

(58) Field of Classification Search

CPC .................................................... C07D 209/20

See application file for complete search history.

(56) References Cited

U.S. PATENT DOCUMENTS

| | | | | |
|---|---|---|---|---|
| 4,073,795 A * | 2/1978 | Batcho | C07D 209/12 | 548/496 |
| 2023/0220001 A1* | 7/2023 | Gruss | C07K 1/113 | 530/317 |

FOREIGN PATENT DOCUMENTS

| | | | |
|---|---|---|---|
| EP | 2138507 A1 | 12/2009 |
| WO | WO 2011/073173 A1 | 6/2011 |
| WO | WO 2018/237153 A1 | 12/2018 |
| WO | WO 2019/030173 A1 | 2/2019 |

OTHER PUBLICATIONS

Chiotellis et al., "Synthesis and Biological Evaluation of $^{18}$F-Labeled Fluoroethoxy Tryptophan Analogues as Potential PET Tumor Imaging Agents," *Molecular Pharmaceutics*, 11(11): 3839-3851 (Jul. 14, 2014).

Li et al., "Synthesis of potent BCRP inhibitor—Ko143," *Tetrahedron Letters*, 49(9): 1480-1483 (Jan. 8, 2008).

European Patent Office, International Search Report in International Patent Application No. PCT/EP2019/084544 (Jan. 28, 2020).

European Patent Office, Written Opinion in International Patent Application No. PCT/EP2019/084544 (Jan. 28, 2020).

Intellectual Property India, Hearing Notice in Indian Patent Application No. 202127019542 (Dec. 4, 2023).

Israel Patent Office, Notice of Deficiencies in Israeli Patent Application No. 282566 (Oct. 22, 2023).

Japan Patent Office, Office Action in Japanese Patent Application No. 2021-528949 (May 7, 2024).

European Patent Office, Communication Pursuant to Article 94(3) EPC in European Patent Application No. 19817704.0 (Jul. 14, 2022).

Intellectual Property India, Examination Report in Indian Patent Application No. 202127019542 (Aug. 3, 2022).

European Patent Office, Communication Pursuant to Article 94(3) EPC in European Patent Application No. 19817704.0 (May 31, 2023).

European Patent Office, Communication Pursuant to Article 94(3) EPC in European Patent Application No. 19817704.0 (Feb. 1, 2024).

Japan Patent Office, Office Action in Japanese Patent Application No. 2021-528949 (Aug. 1, 2023).

IP Australia, Examination Report in Australian Patent Application No. 2019396560 (Jul. 9, 2024).

Davis et al., "A Conjugate of α-Amanitin and Monoclonal Immunoglobulin G to Thy 1.2 Antigen Is Selectively Toxic to T Lymphoma Cells", Science, vol. 213, Sep. 18, 1981, pp. 1385-1388.

Muraoka et al., "Effective Production of Amanitins by Two-Step Cultivation of the Basidiomycete, Galerina fasciculata GF-060", Journal of Bioscience and Bioengineering, vol. 89, No. 1, 2000, pp. 73-76.

Savige et al., "Oxidation of Tryptophan to Oxindolylalanine by Dimethyl Sulfoxide-Hydrochloric Acid", Int. J. Peptide Protein Res., vol. 15, 1980, pp. 285-297.

Schmidtgall et al., "Oligonucleotides with Cationic Backbone and Their Hybridization with DNA: Interplay of Base Pairing and Electrostatic Attraction", Chem. Eur. J., vol. 23, 2017, pp. 1-11.

(Continued)

*Primary Examiner* — Laura L Stockton

(74) *Attorney, Agent, or Firm* — Grüneberg and Myers PLLC

(57) ABSTRACT

The present invention relates to novel methods and compounds for synthesizing amanitin derivatives. The invention in particular relates to methods for synthesizing (S)-6-hydroxy-tryptophan derivatives which can be used as building blocks for synthesizing amanitin derivatives or amatoxin drug conjugates. The invention further relates to intermediate compounds of said synthesis pathways for use in amanitin derivative and amatoxin drug conjugate synthesis, and to the use of particular catalysts suited for mediating said synthesis pathways.

16 Claims, 6 Drawing Sheets

(56) References Cited

OTHER PUBLICATIONS

Wieland et al., "Amatoxins, Phallotoxins, Phallolysin, and Antamanide: The Biologically Active Components of Poisonous Amanita Mushrooms", Critical Reviews in Biochemistry, Dec. 1978, pp. 185-260.
Xue-Wu et al., "Culture conditions and analysis of Amanitins on Amanita spissa", Acta Microbiologica Sinica, vol. 46, No. 3, Jun. 4, 2006, 6 pages with English Abstract.
Zanotti et al., "Structure-toxicity relationships in the amatoxin series", Int. J. Peptide Protein Res., vol. 34, Feb. 7, 1989, pp. 222-228.
Zanotti et al., "Synthesis of analogues of amaninamide, an amatoxin from the white Amanita virosa mushroom", Int. J. Peptide Protein Res., vol. 30, Jan. 30, 1987, pp. 450-459.
Zhang et al., "Production and characterization of Amanitin toxins from a pure culture of Amanita exitialis", FEMS Microbiology Letters, vol. 252, Sep. 15, 2005, pp. 223-228.

* cited by examiner

| | $R_1$ | $R_2$ | $R_3$ | $R_4$ |
|---|---|---|---|---|
| α-amanitin | OH | OH | $NH_2$ | OH |
| β-amanitin | OH | OH | OH | OH |
| γ-amanitin | H | OH | $NH_2$ | OH |
| ε-amanitin | H | OH | OH | OH |
| amanin | OH | OH | OH | H |
| amaninamide | OH | OH | $NH_2$ | H |
| amanullin | H | H | $NH_2$ | OH |
| amanullinic acid | H | H | OH | OH |
| γ-amanin | H | OH | OH | H |
| γ-amaninamide | H | OH | NH2 | H |

(R,S)-Benzyloxycarbonyl-a-phosphono trimethylester
$C_{13}H_{18}NO_7P$

HDP 30.2819
$C_{10}H_{20}NO_7P$

HDP 30.2821
$C_9H_{18}NO_7P$

HDP 30.2822
$C_{16}H_{24}NO_7P$

(R,R)-DIPAMP
$C_{28}H_{28}O_2P_2$

HDP 30.2758
$C_{36}H_{40}BF_4O_2P_2Rh$ 6-(benzyloxy)1H-indole-carbaldehyde
$C_{16}H_{13}NO_2$

HDP 30.2803
$C_{24}H_{19}NO_4$

HDP 30.2824
$C_{38}H_{36}N_2O_7$

HDP 30.2826
$C_{38}H_{38}N_2O_7$

HDP 30.2832
$C_{16}H_{20}N_2O_5$

HDP 30.2834)
$C_{18}H_{22}N_2O_6$

HDP 30.2555 ( cis/trans )
$C_{18}H_{23}N_2O_7$

HDP 30.2824

$C_{38}H_{36}N_2O_7$

HDP 30.2826

$C_{38}H_{38}N_2O_7$

HDP 30.2758

$C_{36}H_{40}BF_4O_2P_2Rh$

(R,R)-Et-DUPHOS ($CF_3SO_3^-$)

$C_{31}H_{48}F_3O_3P_2RhS$

(R,R)-Et-DUPHOS ($BF_4^-$)

$C_{30}H_{48}BF_4P_2Rh$

(R,R)-Et-DUPHOS-Ferrocene ($BF_4^-$)

$C_{34}H_{52}BF_4FeP_2Rh$

(R,R)-Et-DUPHOS-Ferrocene-$Et_2$ ($BF_4^-$)

$C_{38}H_{60}BF_4FeP_2Rh$

(R,R)-DUPHOS-Alkyl ($CF_3SO_3^-$)

$C_{27}H_{48}F_3O_3P_2RhS$

SYNTHESIS OF (S)-6-HYDROXYTRYPTOPHAN AND DERIVATIVES THEREOF

CROSS-REFERENCE TO RELATED APPLICATIONS

This patent application is the U.S. national phase of International Patent Application No. PCT/EP2019/084544, filed Dec. 11, 2019, which claims the benefit of European Patent Application No. 18211747.3, filed Dec. 11, 2018.

FIELD OF THE INVENTION

The present invention relates to novel methods and compounds for synthesizing amanitin derivatives. The invention in particular relates to methods for synthesizing (S)-6-hydroxy-tryptophan derivatives which can be used as building blocks for synthesizing amanitin derivatives or amatoxin drug conjugates. The invention further relates to intermediate compounds of said synthesis pathways for use in amanitin derivative and amatoxin drug conjugate synthesis, and to the use of particular catalysts suited for mediating said synthesis pathways.

BACKGROUND

Amatoxins are cyclic peptides composed of 8 amino acids that are found in *Amanita phalloides* mushrooms (see FIG. 1). Amatoxins specifically inhibit the DNA-dependent RNA polymerase II of mammalian cells, and thereby also the transcription and protein biosynthesis of the affected cells. Inhibition of transcription in a cell causes stop of growth and proliferation. Though not covalently bound, the complex between amanitin and RNA-polymerase II is very tight (KD=3 nM). Dissociation of amanitin from the enzyme is a very slow process, thus making recovery of an affected cell unlikely. When the inhibition of transcription lasts sufficiently long, the cell will undergo programmed cell death (apoptosis).

Amatoxins can be isolated from collected *Amanita phalloides* mushroom fruit bodies, or from pure cultures (Zhang P, et al., FEMS Microbiol Lett. 2005 Nov. 15; 252(2):223-8. Epub 2005 Sep. 15). However, the amounts of amatoxins that can be obtained are rather low (in the range of about 0.3-3 mg/g dry matter from natural fruit bodies, and about 10% thereof from pure culture) and the flexibility for further modifying the naturally occurring amatoxin variants is limited. Alternatively, amatoxins can be obtained from fermentation using a basidiomycete (Muraoka S, and Shinozawa T., J Biosci Bioeng. 2000; 89(1):73-6) or *A. fissa* (Guo X W, et al., 2006 June; 46(3):373-8). Again, yields are low, and flexibility for further modifying the naturally occurring amatoxin variants is limited as well. Finally, amatoxins have been prepared by partial or total synthesis (e.g. Zanotti G, Mähringer C, and Wieland T., lnt J Pept Protein Res. 1987 October; 30(4):450-9; Zanotti G, Wieland T, Benedetti E, Di Blasio 8, Pavone V, and Pedone C., lnt J Pept Protein Res. 1989 September; 34(3):222-8). Alternatively, the use of fully-synthetic routes to amatoxins may offer the supply of larger quantities of amatoxins required for therapeutic uses, and may offer the construction of a variety of novel amatoxin variants by using appropriate starting materials as building blocks.

Naturally occurring amanitins such as α-amanitin, β-amanitin or γ-amanitin are comprising a phenolic hydroxy (—OH) function at the 6'-position of tryptophan, that represents amino acid 4 in the cyclic amanitin octapeptide, which allows for coupling of a linker to the amatoxin (see FIG. 1). Target-binding macromolecules, such as antibodies or aptamers, can then be coupled via said linker in order to generate conjugates, e.g., antibody-drug conjugates. The use of amatoxins as cytotoxic moieties for tumor therapy has already been explored in 1981 by coupling an anti-Thy 1.2 antibody to α-amanitin using a linker attached to the indole ring of tryptophan (Trp, amino acid 4; see FIG. 1) via diazotation (Davis & Preston, 1981, Science 213: 1385-1388).

With the currently explored fully synthetic amanitin compounds, incorporation of a functionalized tryptophan for coupling of linker elements has only been achieved very recently. Prior to that, therefore, linkers were coupled to fully synthetic amanitins predominantly at positions amino acid 1 (aspartic acid) or at the indol-nitrogen (N1) of amino acid 4 (tryptophan). As biologic activity profiles of amanitins coupled via different anchorage positions of the amanitin framework have been shown to be very different, it is of great interest to be able to provide synthetic tryptophan hydroxylated at its 6'-position, i.e. corresponding to the native α-amanitin, β-amanitin or γ-amanitin, as a building block that can be incorporated in the course of amanitin synthesis.

The synthetic introduction of tryptophan into the amanitin framework can be performed by way of the Savige-Fontana reaction (Savige & Fontana, 1980, Int J Pept Protein Res. 15(3): 285-97). According to this reaction, tryptophan is converted into a mixture of Boc-protected cis-2-carboxy-3a-hydroxy-1,2,3,3a,8,8a-hexahydropyrrolo[2,3-b]indol and trans-2-carboxy-3a-hydroxy-1,2,3,3a,8,8a-hexahydropyrrolo[2,3-b]indol and then incorporated into the amino acid sequence of the linear amanitin precursor.

For the fully synthetic production of amanitin, (S)-6-hydroxytryptophan synthesis and synthesis of respective building blocks are of essential importance. In particular, one of these building blocks of essential importance is (S)-6-Acetyloxy-N-tert-butoxycarbonyl-tryptophan (HDP 30.2550).

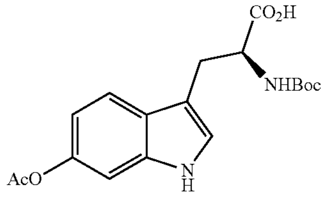

HDP 30.2550

So far, a satisfying and efficient synthesis pathway for (S)-6-hydroxytryptophan and its building blocks has not been described in the prior art. In particular, a synthesis pathway yielding the necessary purity of enantiomers (L or S) of this amino acid derivative has not been available. Different basic options of synthesis could principally be considered. A first option could be the crystallization of the racemic form with chiral auxiliary bases or acids. However, only a maximal yield of 50% could be achieved with this method. A second option is an enzymatic production; employing this method, however, is time-consuming, results are uncertain and reproducibility is weak.

It was hence one object of the present invention to provide an efficient, simple and reproducible method for synthesizing (S)-6-hydroxytryptophan, its derivatives and its building blocks. Preferably, it was one object of the present invention to provide an efficient method for synthesizing (S)-6-Acetyloxy-N-tert-butoxycarbonyl-tryptophan (HDP 30.2550) with a sufficiently high enantiomeric purity.

As one further object of the present invention, the use of said (S)-6-hydroxytryptophan and its derivatives, preferably (S)-6-Acetyloxy-N-tert-butoxycarbonyl-tryptophan, as building blocks for the fully synthetic production of amatoxins should be provided.

These and further objects are met with methods and means according to the independent claims of the present invention. The dependent claims are related to specific embodiments.

SUMMARY OF THE INVENTION

The present invention provides methods for synthesis of (S)-6-hydroxytryptophan, (S)-6-Acetyloxy-N-tert-butoxycarbonyl-tryptophan, and their derivatives and building blocks for their synthesis. The present invention further provides compounds and building blocks for use in synthesizing amanitin or amanitin derivatives or amatoxin-drug conjugates.

The invention and general advantages of its features will be discussed in detail below.

DETAILED DESCRIPTION OF THE INVENTION

Figure 1:
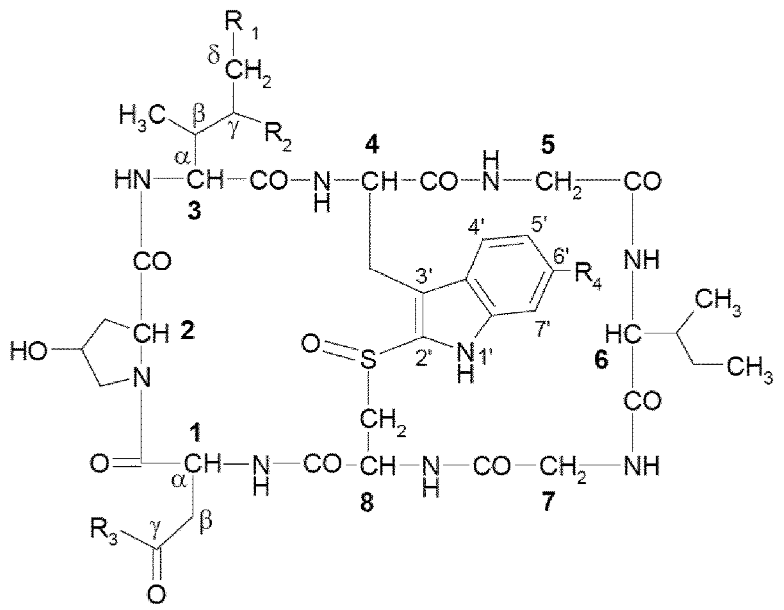
FIG. 1 shows the structural formulae of different amatoxins. The numbers in bold type (1 to 8) designate the standard numbering of the eight amino acids forming the amatoxin. The standard designations of the atoms in amino acids 1, 3 and 4 are also shown (Greek letters a to γ, Greek letters a to 6, and numbers from 1' to 7', respectively).
Figure 2:
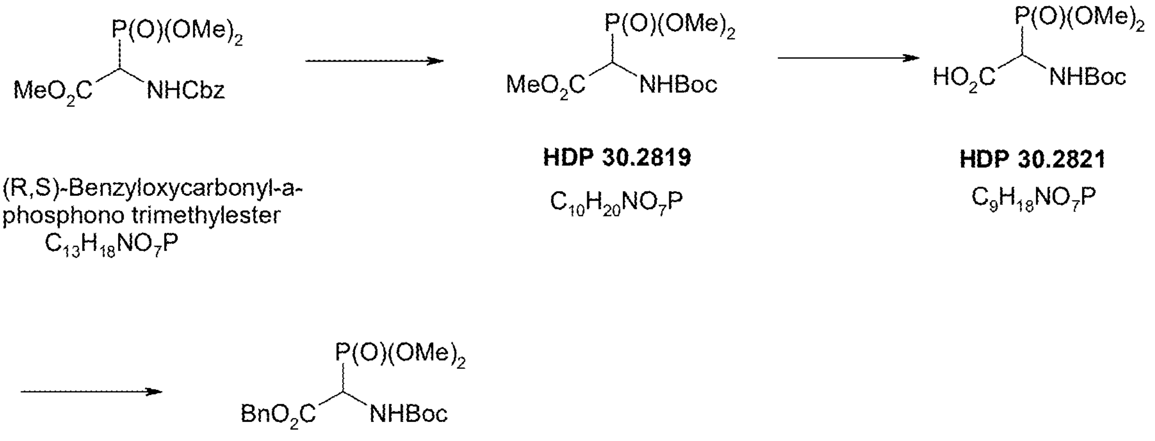
FIG. 2 illustrates the synthesis of compound HDP 30.2822.
Figure 3:
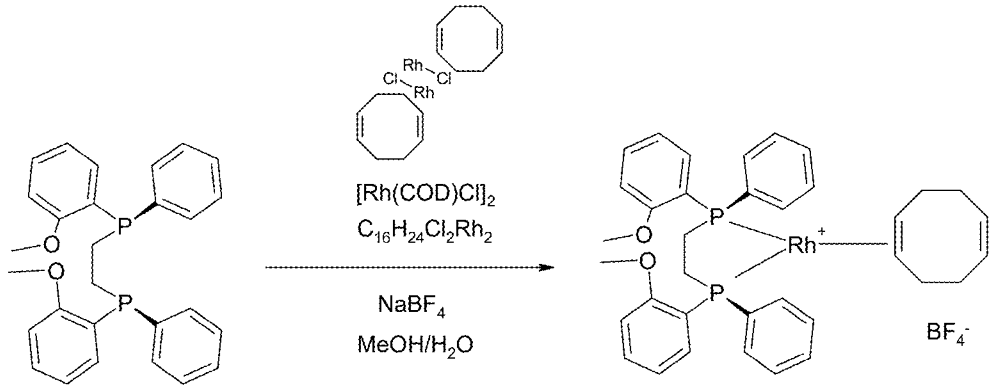
FIG. 3 illustrates the synthesis of compound HDP 30.2758.
Figure 4:
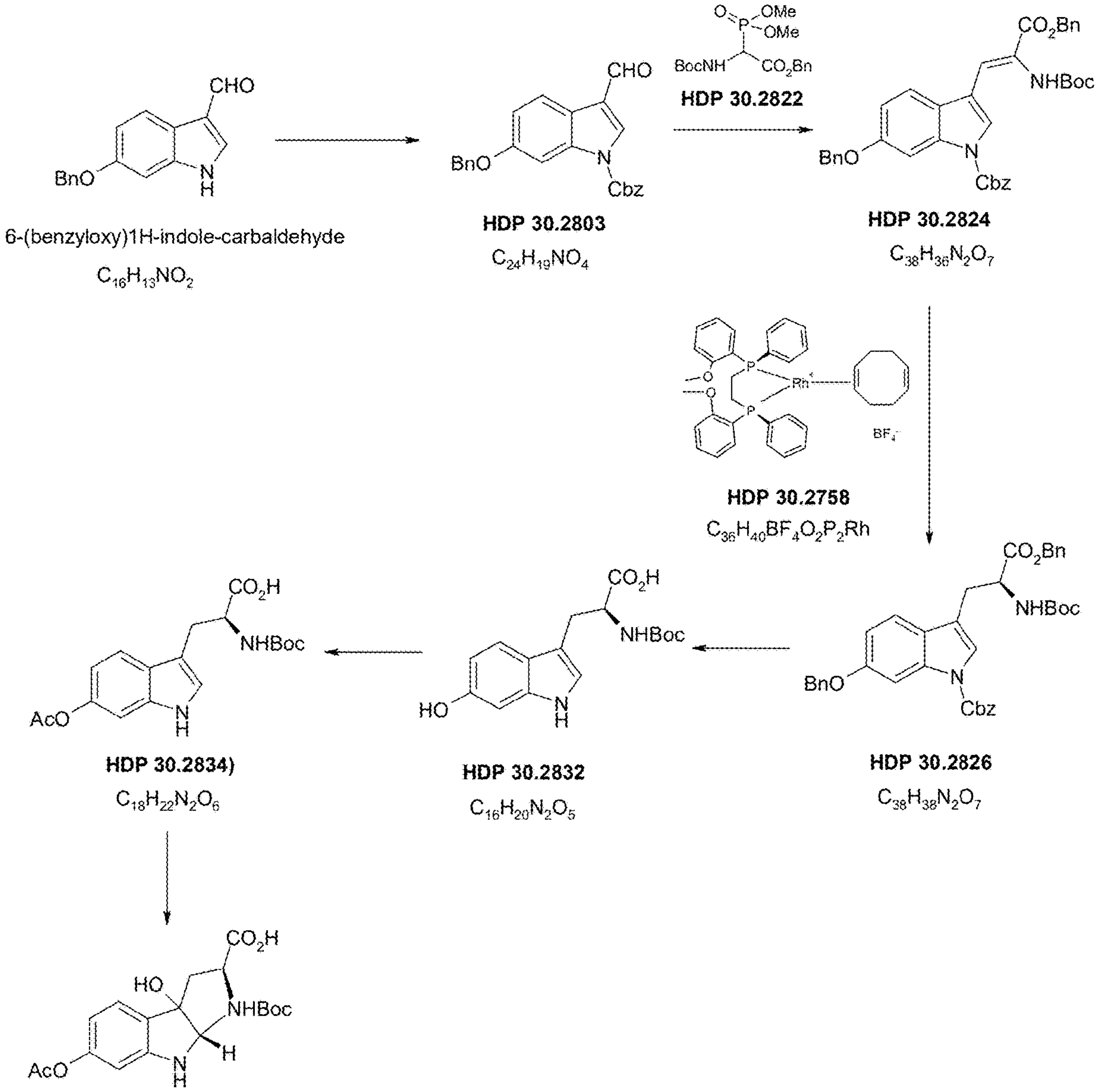
FIG. 4 illustrates the synthesis of compounds HDP 30.2550 and HDP 30.2555.

Before the invention is described in detail, it is to be understood that this invention is not limited to the particular component parts of the means described or process steps of the methods described as such means and methods may vary. It is also to be understood that the terminology used herein is for purposes of describing particular embodiments only, and is not intended to be limiting. It must be noted that, as used in the specification and the appended claims, the singular forms "a", "an", and "the" include singular and/or plural referents unless the context clearly dictates otherwise. It is moreover to be understood that, in case parameter ranges are given which are delimited by numeric values, the ranges are deemed to include these limitation values.

It is further to be understood that embodiments disclosed herein are not meant to be understood as individual embodiments which would not relate to one another. Features discussed with one embodiment are meant to be disclosed also in connection with other embodiments shown herein. If, in one case, a specific feature is not disclosed with one embodiment, but with another, the skilled person would understand that this does not necessarily mean that said feature is not meant to be disclosed with said other embodiment. The skilled person would understand that it is the gist of this application to disclose said feature also for the other embodiment, but that just for purposes of clarity and to keep the specification in a manageable volume this has not been done.

Furthermore, the content of the prior art documents referred to herein is incorporated by reference. This refers, particularly, for prior art documents that disclose standard or routine methods. In that case, the incorporation by reference has mainly the purpose to provide sufficient enabling disclosure, and avoid lengthy repetitions.

A large-scale, industrially feasible production of (S)-6-hydroxytryptophan as comprised in naturally occurring α-, β- and γ-amanitin, and/or chemically protected forms thereof, requires an efficient, simple and reproducible synthesis method. For the first time, the inventors were able to provide such a simple and efficient production method by employing an enantiomer-selective hydrogenation of olefinic amino acid precursors. Using specific chiral catalysts, they surprisingly found that such type of reaction can yield very high enantiomeric purity.

The simple synthetic pathway disclosed yields (S)-6-hydroxytryptophan that is fully identical to the respective native structure. The capability of using said compound and protected forms thereof for industrial large-scale production of amanitins will considerably reduce costs and increase efficiency of, for example, manufacturing synthetic α-, β- or γ-amanitin as well as of amatoxin-based antibody-drug conjugates for therapeutic applications.

According to a first aspect, the present invention relates to a method for synthesis of (S)-6-Acetyloxy-N-tert-butoxycarbonyl-tryptophan (HDP 30.2550) or (S)-6-hydroxytryptophan, wherein said method comprises at least one step of enantiomer-selective hydrogenation of an olefinic precursor compound by use of at least one chiral catalyst.

In one embodiment of the method claimed, said olefinic precursor used for asymmetric hydrogenation is an olefinic unsaturated amino acid precursor. Preferably it is compound HDP 30.2824.

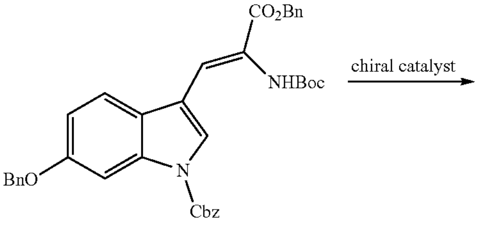

HDP 30.2824

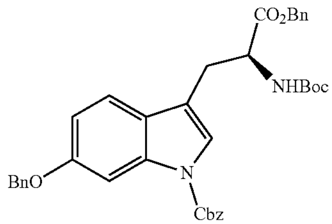

HDP 30.2826

In one embodiment of the method claimed, said olefinic precursor is synthesized by use of the following compound:
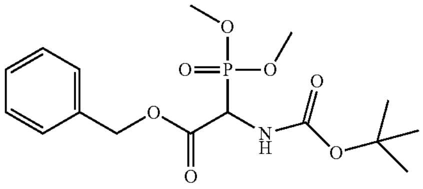
HDP 30.2822
Said olefinic precursor can further be synthesized by use of any of compounds A, B, or C.
A
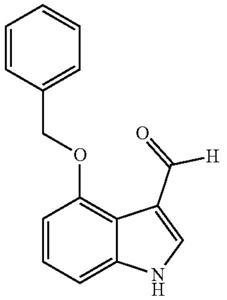
-continued
B
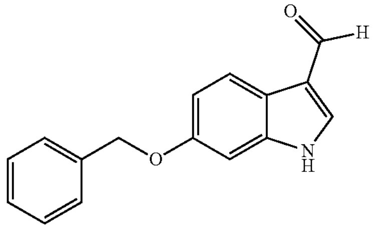
C
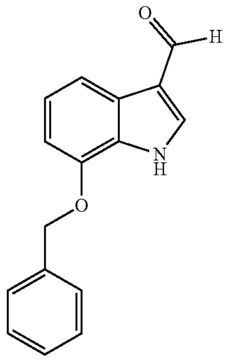
In a further embodiment of the method claimed, said method comprises at least the following steps:
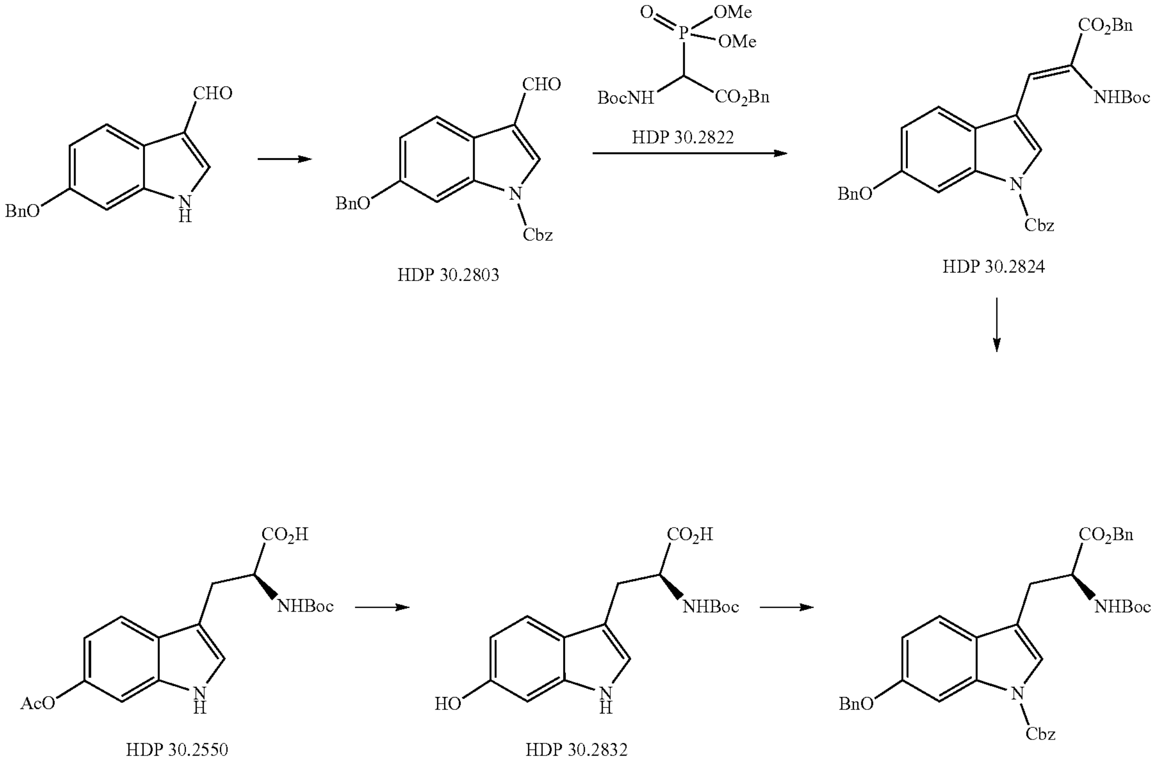
HDP 30.2803
HDP 30.2824
HDP 30.2550
HDP 30.2832
HDP 30.2826

In a still further embodiment of the method claimed, said method comprises at least the following steps:

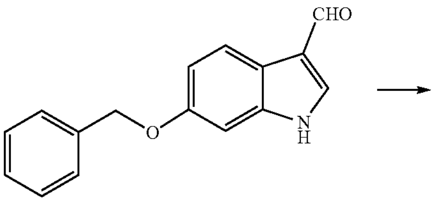

abcr

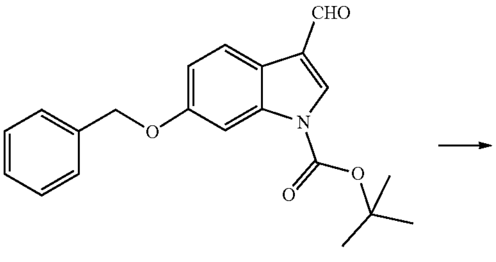

HDP30.2738

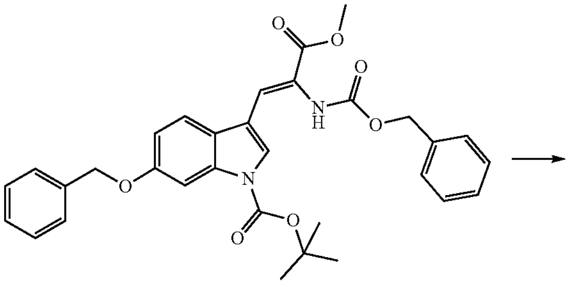

HDP30.2739

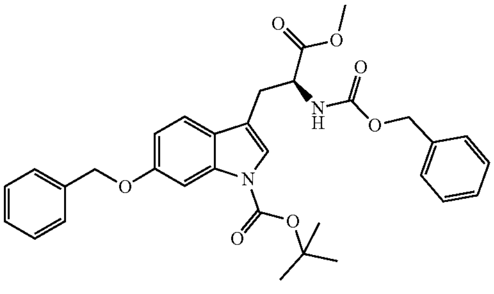

HDP30.2760

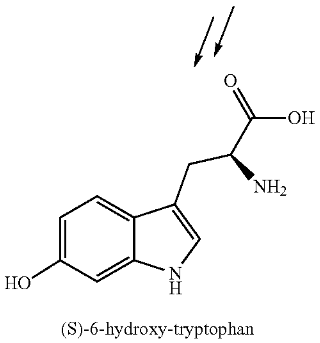

(S)-6-hydroxy-tryptophan

In the context of the present invention the term "amatoxin" includes all cyclic peptides composed of 8 amino acids as isolated from the genus *Amanita* and described in Wieland, T. and Faulstich H. (Wieland T, Faulstich H., CRC Crit Rev Biochem. 5 (1978) 185-260), further all chemical derivatives thereof; further all semisynthetic analogs thereof; further all synthetic analogs thereof built from building blocks according to the master structure of the natural compounds (cyclic, 8 amino acids), further all synthetic or semisynthetic analogs containing non-hydroxylated amino acids instead of the hydroxylated amino acids, further all synthetic or semisynthetic analogs, in which the thioether sulfoxide moiety is replaced by a sulfide, sulfone, thioether, or by atoms different from sulfur, e.g. a carbon atom as in a carbanalog of amanitin. Functionally, amatoxins are defined as peptides or depsipeptides that inhibit mammalian RNA polymerase II. Preferred amatoxins are those with a functional group (e.g. a carboxylic group, an amino group, a hydroxy group, a thiol or a thiol-capturing group) that can be reacted with linker molecules or target-binding moieties as defined below.

In the context of the present invention, the term "amanitins" particularly refers to bicyclic structure that are based on an aspartic acid or asparagine residue in position 1, a proline residue, particularly a hydroxyproline residue in position 2, an isoleucine, hydroxyisoleucine or dihydroxyisoleucine in position 3, a tryptophan or hydroxytryptophan residue in position 4, glycine residues in positions 5 and 7, an isoleucine residue in position 6, and a cysteine residue in position 8, particularly a derivative of cysteine that is oxidized to a sulfoxide or sulfone derivative (for the numbering and representative examples of amanitins, see FIG. 1), and furthermore includes all chemical derivatives thereof; further all semisynthetic analogues thereof; further all synthetic analogues thereof built from building blocks according to the master structure of the natural compounds (cyclic, 8 amino acids), further all synthetic or semisynthetic analogues containing non-hydroxylated amino acids instead of the hydroxylated amino acids, further all synthetic or semisynthetic analogues, in each case wherein any such derivative or analogue is functionally active by inhibiting mammalian RNA polymerase II.

The term "target-binding moiety", as used herein, refers to any molecule or part of a molecule that can specifically bind to a target molecule or target epitope. Preferred target-binding moieties in the context of the present application are (i) antibodies or antigen-binding fragments thereof; (ii) antibody-like proteins; and (iii) nucleic acid aptamers. "Target-binding moieties" suitable for use in the present invention typically have a molecular mass of 40 000 Da (40 kDa) or more.

A "linker" in the context of the present application refers to a molecule that increases the distance between two components, e.g. to alleviate steric interference between the target binding moiety and the amatoxin, which may otherwise decrease the ability of the amatoxin to interact with RNA polymerase II. The linker may serve another purpose as it may facilitate the release of the amatoxin specifically in the cell being targeted by the target binding moiety. It is preferred that the linker and preferably the bond between the linker and the amatoxin on one side and the bond between the linker and the antibody on the other side is stable under the physiological conditions outside the cell, e.g. the blood, while it can be cleaved inside the cell, in particular inside the target cell, e.g. cancer cell or immune cell. To provide this selective stability the linker may comprise functionalities that are preferably pH-sensitive or protease sensitive. Alternatively, the bond linking the linker to the target binding moiety may provide the selective stability. Preferably a linker has a length of at least 1, preferably of 1-30 atoms length (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 atoms) wherein one side of the linker has been reacted with the amatoxin and, the other side with a target-binding moiety. In the context of the present invention, a linker preferably is a $C_{1-30}$-alkyl, $C_{1-30}$-heteroalkyl, $C_{2-30}$-alkenyl, $C_{2-30}$-heteroalkenyl, $C_{2-30}$-alkynyl, $C_{2-30}$-heteroalkynyl, cycloalkyl, heterocycloalkyl, aryl, heteroaryl, aralkyl, or a heteroaralkyl group, optionally substituted. The linker may contain one or more structural elements such as amide, ester, ether, thioether, disulfide, hydrocarbon moieties and the like. The linker may also contain combinations of two or more of these structural elements. Each one of these structural elements may be present in the linker more than once, e.g. twice, three times, four times, five times, or six times. In some embodiments the linker may comprise a disulfide bond. It is understood that the linker has to be attached either in a single step or in two or more subsequent steps to the amatoxin and the target binding moiety. To that end the linker to be will carry two groups, preferably at a proximal and distal end, which can (i) form a covalent bond to a group, preferably an activated group on an amatoxin or the target binding-peptide or (ii) which is or can be activated to form a covalent bond with a group on an amatoxin. Accordingly, if the linker is present, it is preferred that chemical groups are at the distal and proximal end of the linker, which are the result of such a coupling reaction, e.g. an ester, an ether, a urethane, a peptide bond etc. The presence of a "linker" is optional, i.e. the toxin may be directly linked to a residue of the target-binding moiety in some embodiments of the target-binding moiety toxin conjugate.

According to a second aspect, the present invention relates to (S)-6-Acetyloxy-N-tert-butoxy-carbonyl-tryptophan (HDP 30.2550), (S)-6-hydroxy-tryptophan or any of the precursor compounds according to the present invention for use in synthesis of amanitin or amanitin derivatives or amatoxin-drug conjugates.

In one embodiment, the present invention relates to a dehydro-amino acid compound selected from the group consisting of compounds I, II, III, IV and V,

I

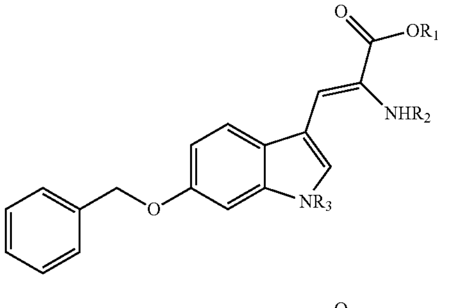

II

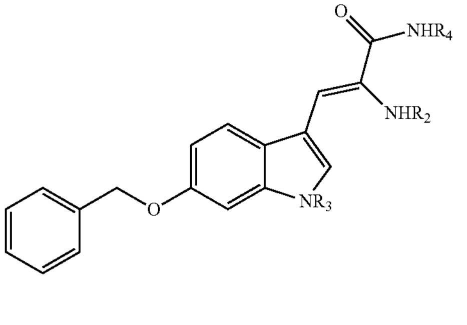

-continued

III

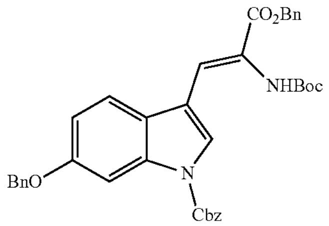

IV

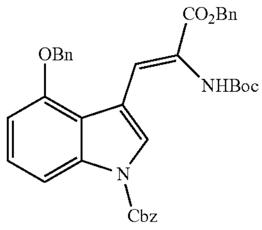

V

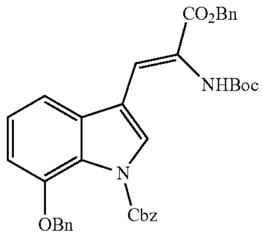

wherein

R1 is selected from: H, alkyl, alkenyl, aryalkyl optional substituted

R2 is selected from: Boc, Cbz, N protecting groups

R3 is selected from: Boc, Cbz, N protecting groups

R4 is an amino acid residue for use in synthesis of amanitin or amanitin derivatives or amatoxin-drug conjugates.

Compounds III, IV and V are preferred.

Figure 5:
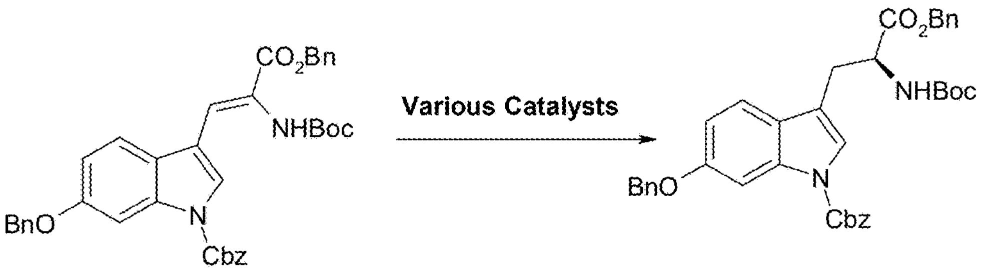
FIG. 5 shows structural compositions of catalysts used for the conversion of HDP 30.2824 to HDP 30.2826.
Figure 5:
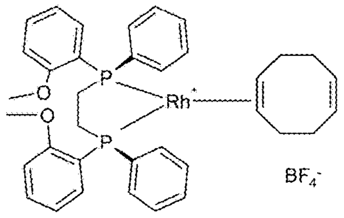
Figure 5:
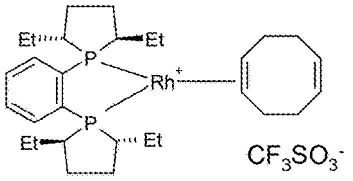
Figure 5:
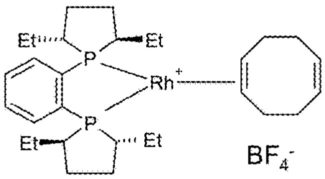
Figure 5:
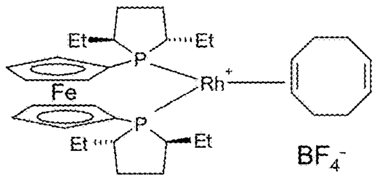
Figure 5:
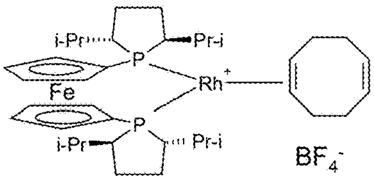
Figure 5:
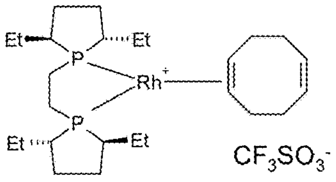
Figure 6:
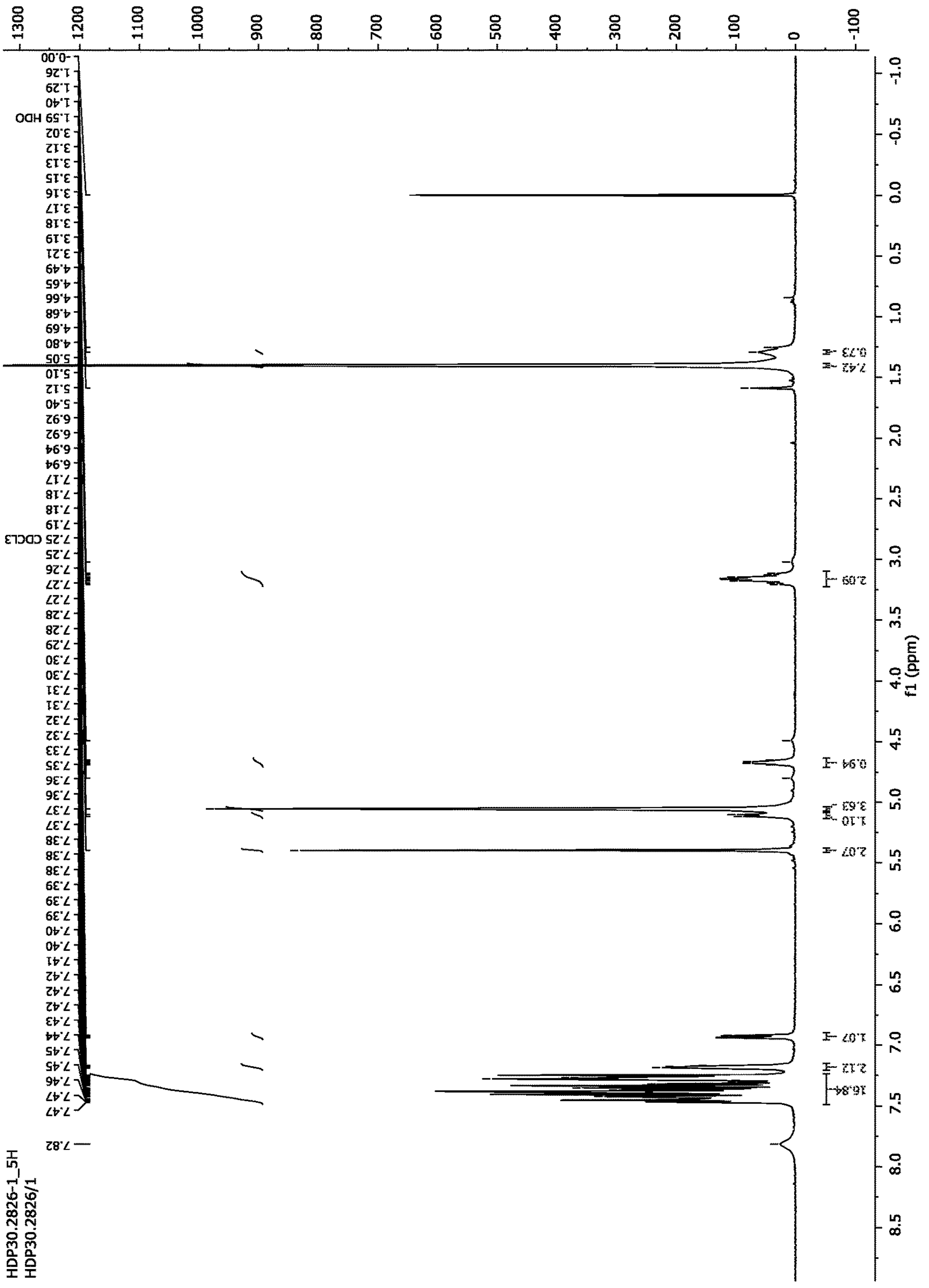
FIG. 6 shows 1H NMR spectroscopy results from compound HDP 30.2826 (400 MHz, $CDCl_3$, δ=ppm).
Figure 7:
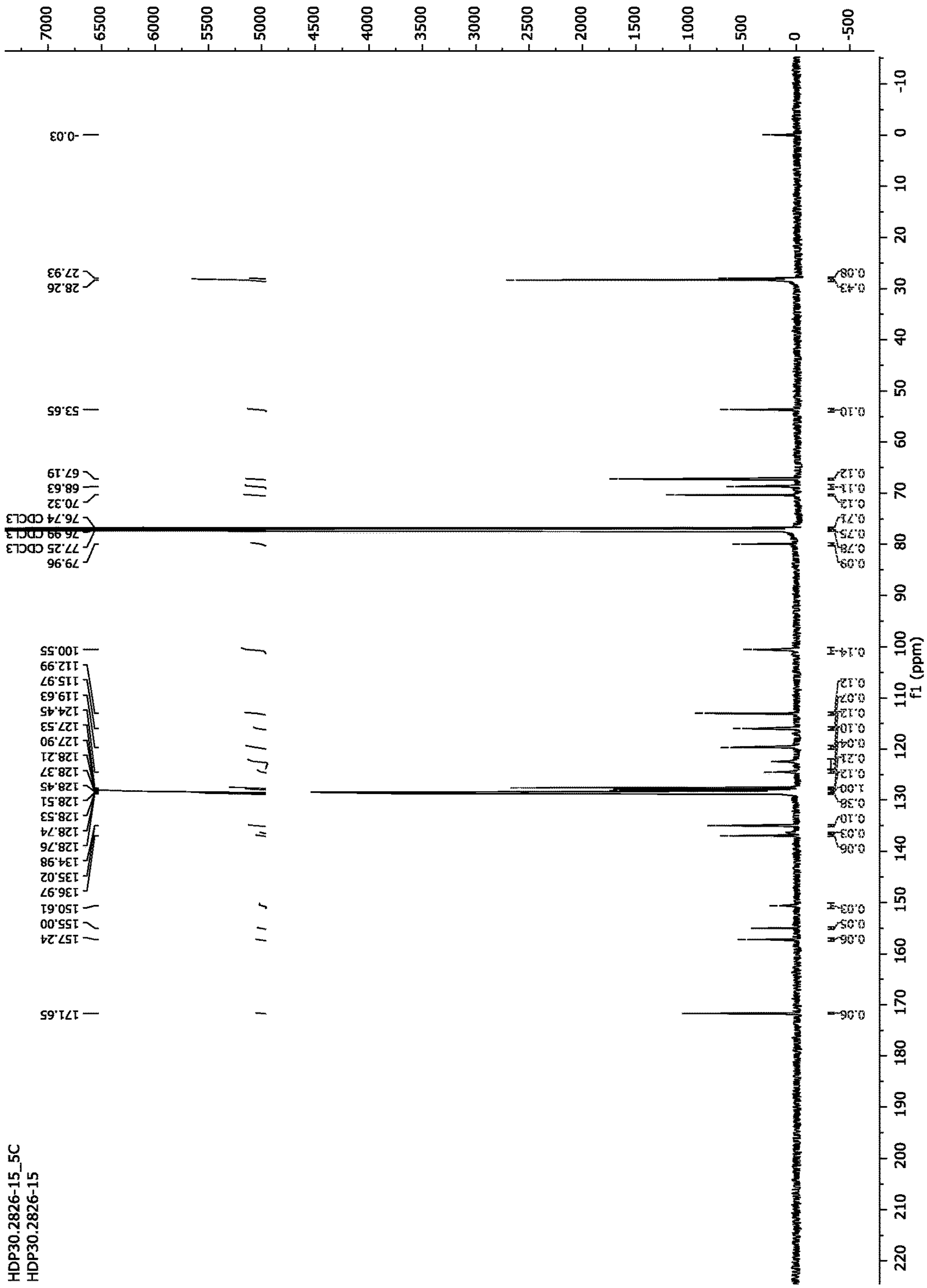
FIG. 7 shows 13C NMR spectroscopy results from compound HDP 30.2826 (100 MHz, $CDCl_3$, δ=ppm).

Furthermore, the inventors surprisingly found that from a larger panel of catalytic compounds tested for asymmetric hydrogenation (see Table 1, FIG. 5), the catalyst Cyclooctadiene-1,5-[(R,R)-DIPAMP] rhodium tetrafluoroborate, HDP 30.2758, yielded the highest enantiomeric purity which was >98%).

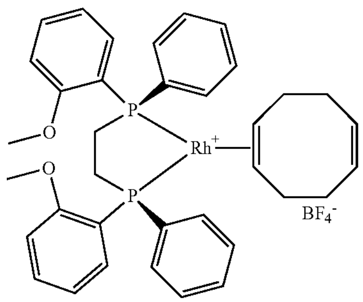

HDP 30.2758

It was found that only the catalyst HDP 30.2758 yielded a very high purity of more than 98% of (S)-enantiomers. All other catalysts except (R,R)-Et-DUPHOS ($BF_4$–) yielded considerably lower (S)-enantiomer purities of 50-70%. In addition, the overall absolute compound turnover and yield rates were much poorer than with HDP 30.2758.

The catalysts tested for asymmetric hydrogenation and respective (S)-enantiomer purity levels are compiled in Table 1.

TABLE 1

Comparative Assessment of various catalysts used for enantiomer-selective hydrogenation

| Catalyst # | Identity | Purity Level |
|---|---|---|
| 1 | HDP 30.2758 | >98% chiral purity |
| 2 | (R,R)-Et-DUPHOS ($CF_3SO_{3-}$) | no conversion |
| 3 | (R,R)-Et-DUPHOS ($BF_{4-}$) | 90-95% chiral purity |
| 4 | (R,R)-DuPhos-Ferrocene ($BF_{4-}$) | 65% chiral purity |
| 5 | (R,R)-DuPhos-Ferrocene-$Et_2$ ($BF_{4-}$) | 55% chiral purity |
| 6 | (R,R)-DuPhos-Alkyl ($CF_3SO_{3-}$) | 73% chiral purity |
| 7 | (R,R)-Phenyl-DuPhos-Alkyl ($BF_{4-}$) | <60% chiral purity |

Thus according to a third aspect, the present invention relates to the use of a compound selected from the group consisting of compound HDP 30.2758, (R,R)-Et-DUPHOS ($BF_{4-}$), (R,R)-DuPhos-Ferrocene ($BF_{4-}$), (R,R)-DuPhos-Ferrocene-$Et_2$ ($BF_{4-}$), (R,R)-DuPhos-Alkyl ($CF_3SO_{3-}$), and (R,R)-Phenyl-DuPhos-Alkyl ($BF_{4-}$) as catalyst for hydrogenation in the following reaction:

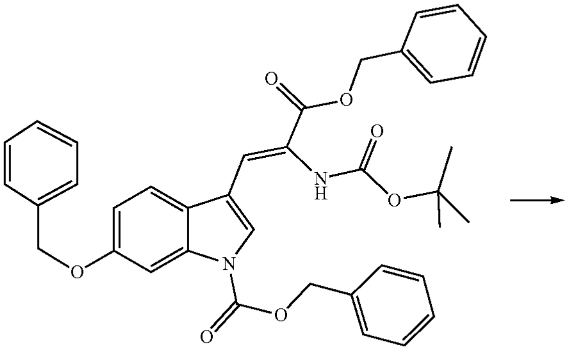

HDP 30.2824

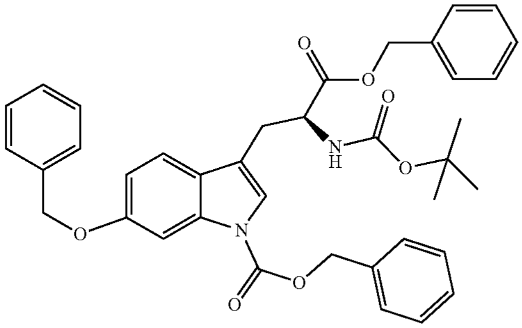

HDP 30.2826

According to this aspect, the present invention preferably relates to the use of the chiral catalysts cyclooctadiene-1,5-[(R,R)-DIPAMP] rhodium tetrafluoro-borate (HDP 30.2758) or (R,R)-Et-DUPHOS ($BF_{4-}$), most preferably of the chiral catalyst cyclooctadiene-1,5-[(R,R)-DIPAMP] rhodium tetrafluoro-borate (HDP 30.2758), as catalyst for hydrogenation in the following reaction:

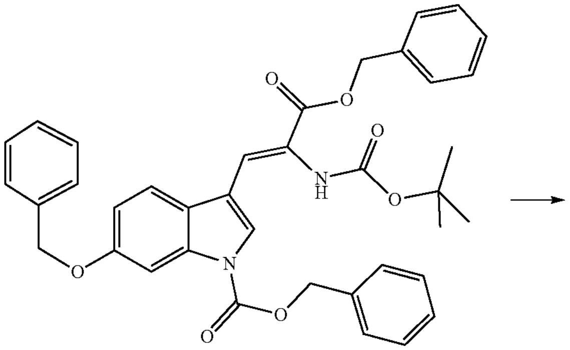

HDP 30.2824

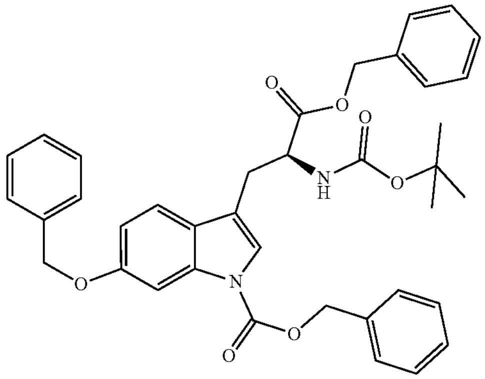

HDP 30.2826

The incorporation of tryptophan derivatives as building blocks into amanitin precursors has been described before in PCT/EP2018/071268, the content of which is incorporated herein by reference. Such as HDP 30.2115 can be synthesized by incorporation of unsubstituted Hpi building block into an amanitin peptidic precursor molecule in order to yield synthetic amantitin, the 6-hydroxy-substituted building block HDP 30.2555 can be used for synthesis of 6-hydroxy-substituted amanitins according to the present invention.

EXAMPLES

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

Example 1: Synthesis of the Phosphonium Precursor (Building Block) HDP 30.2822

The synthesis of the phosphonium precursor (building block) HDP 30.2822 was performed as described (CHEMISTRY A European Journal, 2018, Vol. 24, Issue 7, pp 1544-1553):

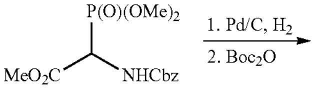

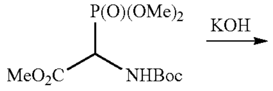

HDP 30.2819

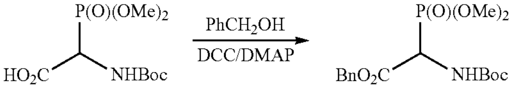

HDP 30.2821 HDP 30.2822

Example 1.1: Preparation of (R,S)-Boc-α-phosphonoglycine Trimethyl Ester HDP 30.2819

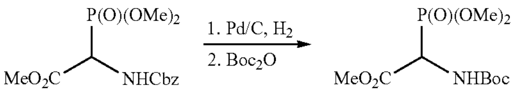

HDP 30.2819

5.0 g (15.1 mmol) (R,S)—N-Cbz-phosphonoglycine trimethyl ester (CAS: 88568-95-0) was hydrogenated with 1.4 g 10% Pd.C in 100 ml methanol at 1 atm until the reaction was complete by TLC (chloroform/methanol 15:1). The reaction was complete in 3 hours. The catalyst was filtered off over a plug of Celite® (diatomaceous earth) and the methanolic solution of the free amine was concentrated in vacuo to a colorless oil (2.9 g). The crude oil was used for the next step without purification.

2.9 g crude hydrogenation product was dissolved in 20 ml dichloromethane and treated with 3.23 ml (15.1 mmol) di-tert-butyl dicarbonate ($Boc_2O$). After 17 hours stirring at ambient temperature under argon, the reaction mixture was concentrated to dryness. The remaining colorless oil crystalizes to a white solid (4.3 g). The crude HDP 30.2819 was used for the next step without purification.

Example 1.2: Preparation of (R,S)—N-Boc-α-phosphonoglycine Trimethyl Ester HDP 30.2821

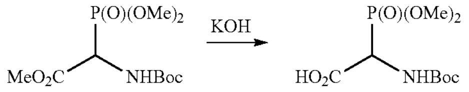

HDP 30.2819 HDP 30.2821

4.3 g (assumed 14.3 mmol) crude HDP 30.2819 was dissolved in 10 ml 1,4-dioxane and rapidly treated under argon and room temperature with 14.5 ml 1 N KOH. After 85 minutes, the reaction mixture was diluted with 36 ml water and extracted with 35 ml ethyl acetate. The ethyl acetate extract was discarded and the aqueous solution acidified to pH 3 by dropwise addition of 1 N HCl. The reaction mixture was extracted with 60 ml ethyl acetate (2×), and dried over $MgSO_4$. The resulting white solid, 2.1 g of HDP 30.2821, was dried in vacuo and used directly without purification for the next reaction step.

Mp: 148-150° C. (Lit. JACS 111, 6244, 1989 mp: 154-155° C.).

MS ($ESI^-$) found: 282.00 $[M-H]^-$; calc.: 283.08 ($C_9H_{18}NO_7P$).

MS ($ESI^-$) found: 238.17 $[M-CO_2]^-$.

Example 1.3: Preparation of (R,S)—N-Boc-α-dimethylphosphono)-glycine Benzyl Ester HDP 30.2822

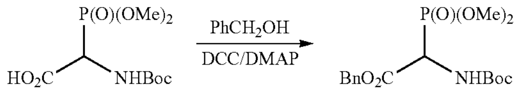

HDP 30.2821 HDP 30.2822

2.0 g (7.1 mmol) HDP 30.2821 in 90 ml dry dichloromethane was treated with 4.6 ml (44.1 mmol) benzylic alcohol 230 mg DMAP and 2.2 g (10.6 mmol) DCC dissolved in 7 ml dichloromethane. The reaction mixture was stirred under argon at ambient temperature for 24 hours. Then the urea was filtered off and the organic phase washed with 5% citric acid and dried over $MgSO_4$. After the evaporation of the dichloromethane, the remaining semi-solid was taken off in ethyl acetate and filtered again to remove additional urea. The crude product was purified by flash chromatography on a 330 g silica gel column (detection wave length 254 nm) with a gradient of n-hexane to n-hexane/ethyl acetate (1:2) and gave after evaporation 1.94 g (73%) HDP 30.2822 as a white solid.

MS ($ESI^+$) found: 373.92 $[MH]^+$; calc.: 373.13 ($C_{16}H_{242}O_7P$).

MS ($ESI^+$) found: 396.17 $[M+Na]^+$.

Example 2: Synthesis of (S)-6-Acetyloxy-N-tert-butoxycarbonyl-tryptophan HDP 30.2550 as Precursor of HDP 30.2555 (Hydroxy-Hpi)

The synthesis pathway is summarized in the following synthesis scheme.

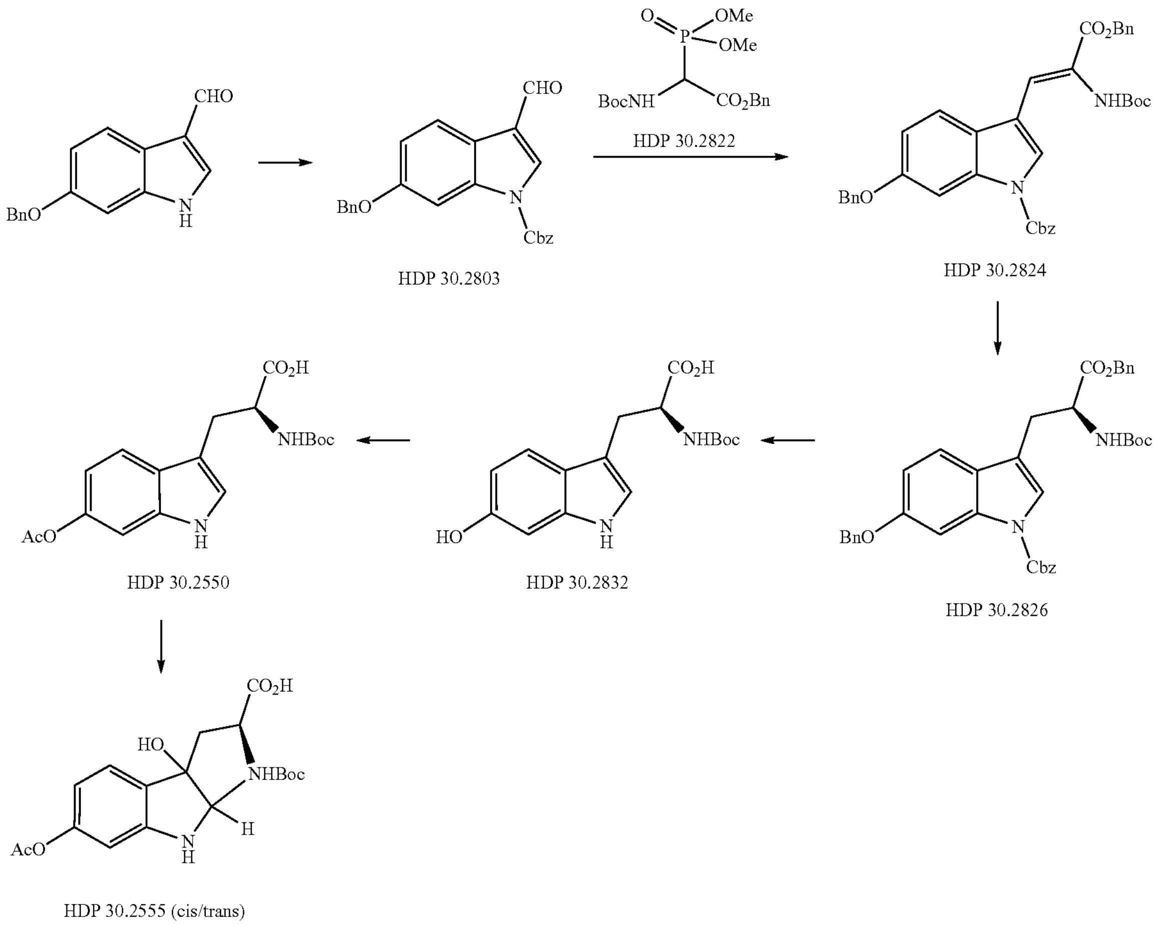

HDP 30.2803

HDP 30.2824

HDP 30.2826

HDP 30.2832

HDP 30.2550

HDP 30.2555 (cis/trans)

Example 2.1: Preparation of N-Cbz-6-benzyloxy-indole-3-aldehyde HDP 30.2803

The starting material 6-Benzyloxyindole-3-aldehyde for the synthesis is commercially available or can by produced by Vilsmeier reaction in high yields, starting from 6-Benzyloxyindole.

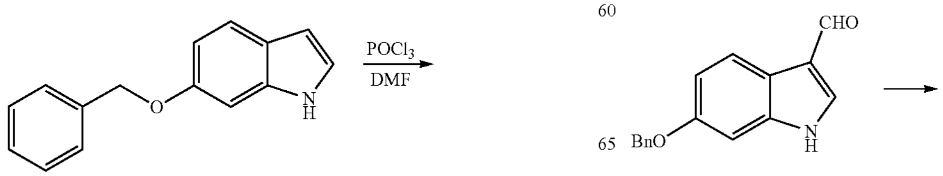

-continued

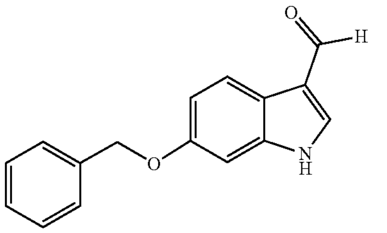

No chromatography is required for purification.

-continued

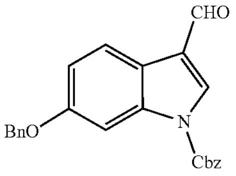

HDP 30.2803

Triethylamine (1.66 mL, 11.94 mmol, 1.50 eq) was added via syringe to a solution of 6-benzyloxy-3-formyl indole (2.00 g, 7.96 mmol, 1 eq) and (DMAP) 4-dimethylamino-pyridine (97.23 mg, 796 μmol) in dichloromethane (20 ml) at 23° C. Benzyl chloroformate (1.45 mL, 10.35 mmol, 1.30 eq) was added dropwise to the solution via syringe. After 1 h, another portion of benzyl chloroformate (223 μL, 1.59 mmol, 0.20 eq) was added via syringe. After 95 min, the reaction mixture was diluted with dichloromethane (85 mL) and washed with saturated aqueous sodium bicarbonate solution (85 mL). The aqueous layer was further extracted with dichloromethane (2×20 mL). The combined organic layers were washed with aqueous hydrogen chloride (1 N, 85 mL) and the resulting aqueous layer was extracted with dichloromethane (2×20 mL). The combined organic layers were dried over anhydrous $MgSO_4$, were filtered, and were concentrated under reduced pressure. The crude product was purified by flash chromatography on a 330 g silica gel column (detection wave length 254 nm) with a gradient of n-hexane/ethyl acetate 4:1 to n-hexane/ethyl acetate (1:1) and gave after evaporation 2.33 g (76%) HDP 30.2803 as a white solid.

$^1$H-NMR (400 MHz, $CDCl_3$, δ=ppm)

δ=5.05 (s, 2H, $OCH_2$); 5.47 (s, 2H, $COOCH_2$); 7.06-8.14 (m, Ar—H, 14H); 10.01 (s, 1H, CHO)

Example 2.2: Preparation of [6-Benzyloxy-1H-(benzyloxycarbonyl)-3-indole]-2-(tert-butyloxycarbonylamino)-acrylic Acid Benzyl Ester HDP 30.2824

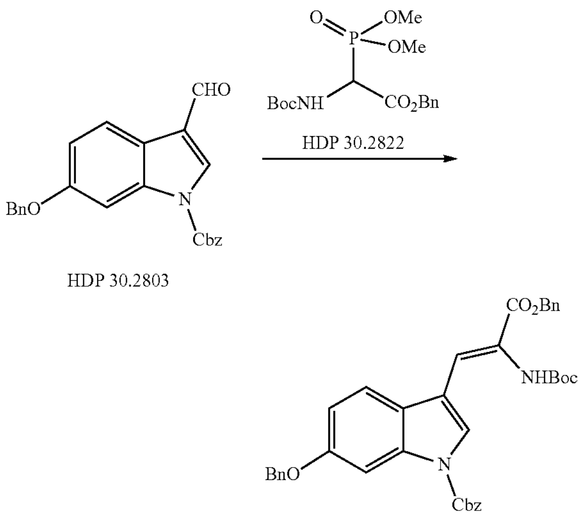

HDP 30.2803

HDP 30.2824

1.90 g (5.09 mmol) (R,S)—N-Boc-α-dimethylphosphono)-glycine benzyl ester HDP 30.2822 was suspended under argon in 8 ml dichloromethane. 0.705 ml (4.73 mmol) DBU was added. After 10 minutes stirring, 1.66 g (4.31 mmol) N-Cbz-6-benzyloxy-indole-3-aldehyde HDP 30.2803 in 4.7 ml dichloromethane was slowly added. The reaction mixture was stirred for 5 hours and the solvent was evaporated under reduced pressure. The residue was dissolved in 120 ml ethyl acetate, and the organic solution was washed 2 times with 50 ml 1N HCl and 50 ml brine, dried over $MgSO_4$ and concentrated under reduced pressure to give 2.70 g of crude material. The crude product was purified by flash chromatography on a 330 g silica gel column (detection wave length 254 nm) with a gradient of n-hexane to n-hexane/ethyl acetate (1:1) and gave after evaporation 2.00 g (73%) HDP 30.2824 as a white solid.

MS (ESI$^+$) found: 632.92 [MH]$^+$; calc.: 632.25 ($C_{38}H_{36}N_2O_7$).

MS (ESI$^+$) found: 655.25 [M+Na]$^+$.

Example 2.3: Preparation of (S)-6-Benzyloxy-N-tert-butoxycarbonyl-1-Cbz-L-Tryptophan Benzyl Ester HDP 30.2826

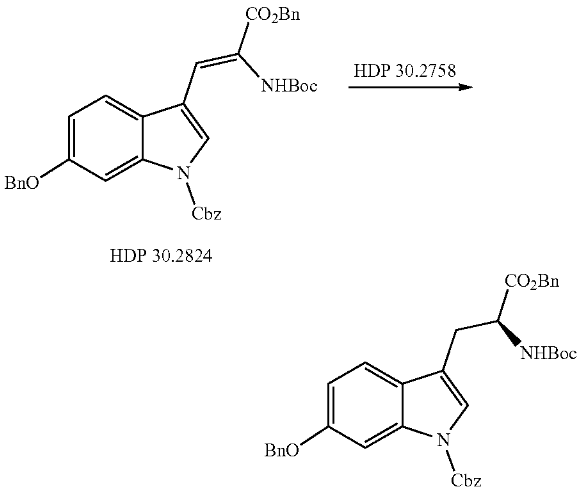

HDP 30.2824

HDP 30.2826

Example 2.3.1: Synthesis of cyclooctadiene-1,5-[(R,R)-DIPAMP] Rhodium Tetrafluoroborate Catalyst HDP 30.2758

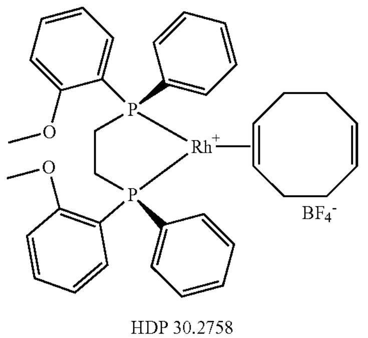

HDP 30.2758

97.0 mg (0.20 mmol) Bis(cyclooctadiene-1,5)-dichloro dirhodium $[Rh(COD)Cl]_2$ (CAS:12092-47-6. Alfa Aesar) was added to a suspension of 180.0 mg (0.39 mmol) (R,R)-DIPAMP (CAS:55739-58-7, Alfa Aesar) in 2.0 ml methanol/water (1.5 ml/0.5 ml). The orange colored slurry, stirred for 1 hour under argon, gave an orange solution. The complex was precipitated by adding slowly (over 30 minutes) a solution of 65.0 mg (0.6 mmol) sodium tetrafluoroborate in 0.5 ml water. After 2.5 hours stirring at room temperature the orange crystals were filtered off, washed twice with small portions of water, and dried at high vacuum. 240 mg (81%) of the catalyst cyclooctadiene-1,5-[(R,R)-DIPAMP]rhodium tetrafluoroborate HDP 30.2758 was obtained as a bright yellow powder. The catalyst was used without further purification.

Example 2.3.2: Synthesis of (S)-6-Benzyloxy-N-tert-butoxycarbonyl-1-Cbz-L-tryptophan Benzyl Ester HDP 30.2826

A 250 ml stainless steel autoclave was charged with 35.0 mg (0.08 mmol) cyclooctadiene-1,5-[(R,R)-DIPAMP]rhodium tetrafluoroborate HDP 30.2758, 1000 mg (1.8 mmol) [6-Benzyloxy-1H-(benzyloxycarbonyl)-3-indole]-2-(tert-butyloxycarbonylamino)-acrylic acid benzyl ester HDP 30.2824 in 40 ml dry methanol/15 ml dichloromethane. After four vacuum/Ar and $H_2$ cycles, the reaction was pressurized to an initial pressure of 12 bar. The reaction was allowed to proceed for 4 days at ambient temperature. After the evaporation of the solvent, the crude product was purified by flash chromatography on a 220 g silica gel column (detection wave length 254 nm) with n-hexane/ethyl acetate (3:1) and gave after evaporation 0.79 g (79%) HDP 30.2826 as a white powder.

MS ($ESI^+$) calc.: 634.26 ($C_{38}H_{38}N_2O_7$)

MS ($ESI^+$) found: 657.33 $[M+Na]^+$;

Example 2.4: Preparation of N-tert-butoxycarbonyl-(S)-tryptophan HDP 30.2832

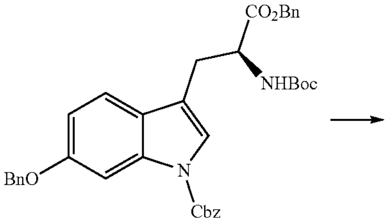

HDP 30.2826

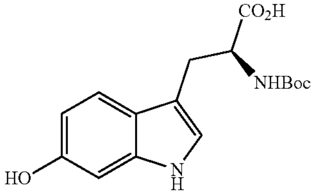

HDP 30.2832

700 mg (1.10 mmol) (S)-6-Benzyloxy-N-tert-butoxycarbonyl-1-Cbz-tryptophan benzyl ester HDP 30.2826 was hydrogenated with 100 mg Pd—C 10% in a mixture of 7 ml ethyl acetate and 4 ml methanol. After 3 hours hydrogenation (TLC control with chloroform/methanol 19:1+1% AcOH) at room temperature and 1 atm., the catalyst was removed by filtering over a plug of Celite®. The solvent was removed, and the remaining crude residue, 378 mg of HDP 30.2832, was used for the next step without purification.

Example 2.5: Preparation of (S)-6-Acetyloxy-N-tert-butoxycarbonyl-tryptophan HDP 30.2550

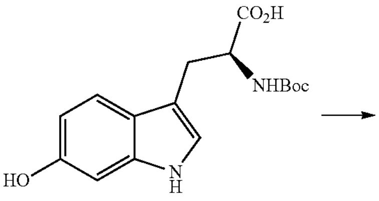

HDP 30.2832

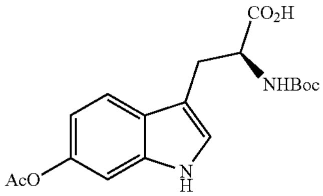

HDP 30.2550

378 mg crude HDP 30.2832 (assumed 1.10 mmol) was dissolved in 2.21 ml 1 NaOH. Under argon and ambient temperature, 208.5 µl (2.20 mmol) acetic anhydride was added at once. The mixture was stirred for 3.5 hours and acidified with 5% citric acid. The reaction mixture was extracted 3x with ethyl acetate, and the combined organic phases washed with 5% sodium chloride and dried over $MgSO_4$. Filtration and evaporation to dryness gave 380 mg crude material. The crude product was purified by flash chromatography on a 120 g silica gel column (detection wave length 254 nm) with a gradient of dichloromethane+2% AcOH/dichloromethane/methanol (15:1)+2% AcOH and gave after evaporation 270 mg (68%) HDP 30.2550 as a white solid.

MS ($ESI^-$) found: 361.17 $[M-H]^-$; calc.: 362.15 ($C_{18}H_{22}N_2O_6$).

MS ($ESI^-$) found: 723.08 $[2M-H]^-$.

Example 3: Preparation of (S)-6-Hydroxy-Tryptophan by Asymmetric Hydrogenation of Dehydro Amino Acid
The synthesis pathway is summarized in the following synthesis scheme.
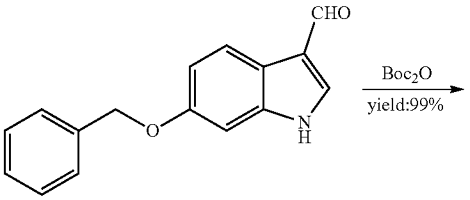
abcr
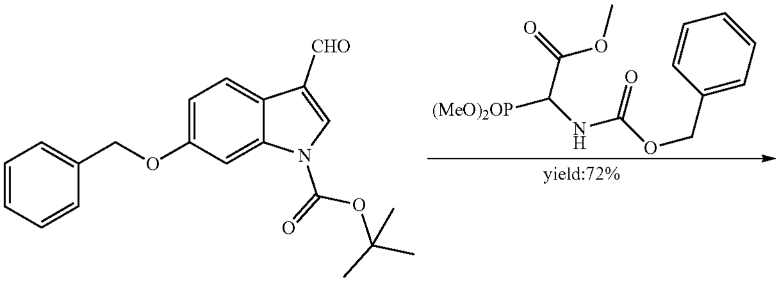
HDP30.2738
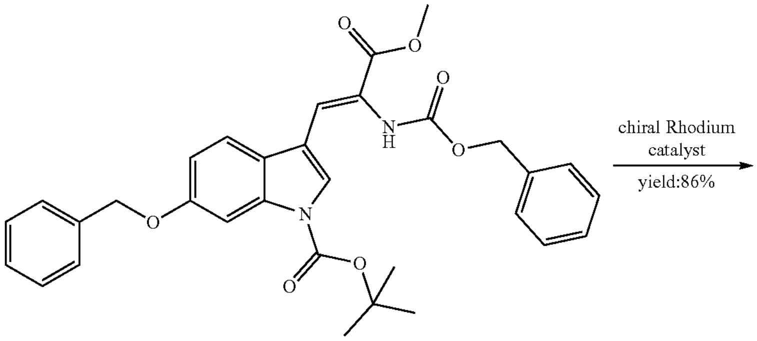
HDP30.2739
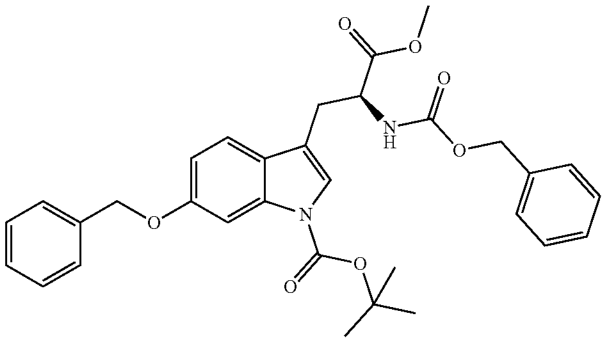
HDP30.2738
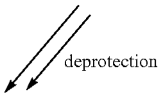

-continued

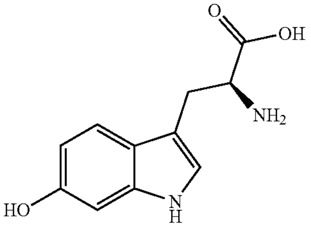

(S)-6-hydroxy-tryptophan

Example 3.1: Preparation of 6-Benzyloxy-1H-indole-3-carbaldehyde

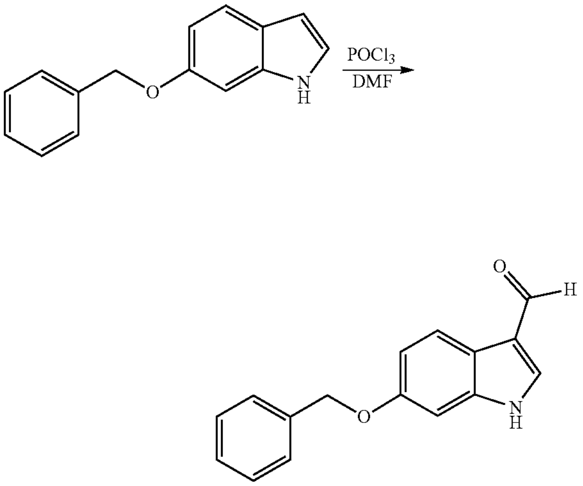

To a stirred solution of phosphorus oxychloride (10.0 mL, 107.0 mmol) in DMF (35 mL) a solution of 6-benzyloxy-indole (22.3 g, 100.0 mmol) in DMF (25 mL) was added at room temperature. After 45 min, the reaction mixture was poured into ice-water (200 mL). To this mixture solid NaOH (19.0 g, 475.0 mmol) and water (100 mL) was added. After 30 minutes additional water (200 ml) was added and the whole mixture was refluxed for 3 minutes. The precipitate was collected, washed with 5 portions of 50 ml cold water and dried to give 24.8 g (98.8%) 6-Benzyloxy-1H-indole-3-carbaldehyde as a white powder. The compound was identical with reference material and sufficiently pure for the next reaction.

Example 3.2: Preparation of 6-Benzyloxy-1H-1-tert-butoxycarbonyle-indole-carbaldehyde HDP 30.2738

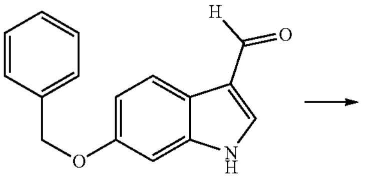

-continued

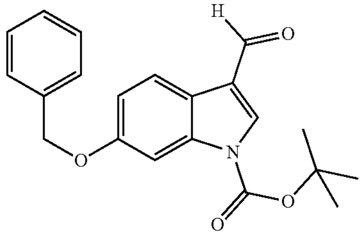

HDP 30.2738

10.0 g (39.8 mmol) 6-Benzyloxy-1H-indole-3-carbaldehyde was suspended in 100 ml dichloromethane and treated with 0.56 g (4.5 mmol) 4-dimethylaminopyridine DMAP and 10.5 g (47.3 mmol) di-tert-butyl dicarbonate $Boc_2O$ dissolved in 10 ml dichloromethane. After stirring for 2 hours, 100 ml 1N $KHSO_4$ was added and dichloromethane was evaporated. The aqueous layer was extracted with several portions of diethyl ether (2×200 ml) and the combined organic extracts were washed with 250 ml 1N $KHSO_4$, 250 ml 1N $NaHCO_3$ and 250 ml brine. The organic layer was dried over $MgSO_4$ and concentrated under reduced pressure to give 12.0 g (86%) red-brownish powder. The compound was sufficiently pure for the next reaction step.

Example 3.3: Preparation of 3-[6-Benzyloxy-1H-(1-tert-butoxycarbonyl)-3-indole]-2-(benzyloxycarbonylamino)-acrylic Acid Methyl Ester HDP 30.2739

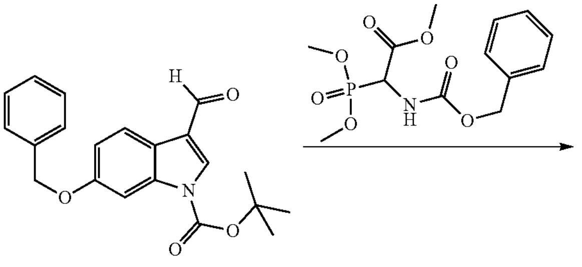

HDP 30.2738

-continued

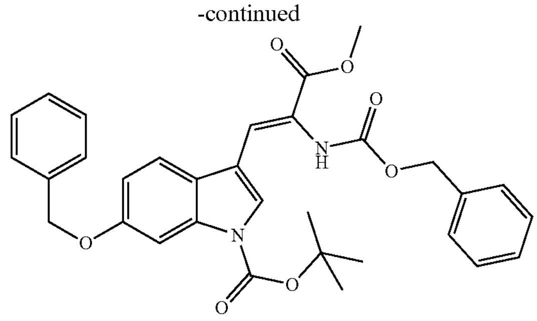

HDP 30.2739

5.12 g (15.44 mmol) (R,S)-Benzyloxycarbonyl-6-phosphono-glycine trimethylester (CAS: 88568-95-0, Alfa Aesar) was dissolved under argon in 18 ml dichloromethane. 2.14 ml (14.31 mmol) DBU was added. After 10 minutes stirring, 4.60 g (13.07 mmol) 6-Benzyloxy-1H-1-tert-butyloxycarbonyle-indole-3-carbaldehyde HDP 30.2738 in 14 ml dichloromethane was added slowly. The reaction mixture was stirred for 6 hours and the solvent was evaporated under reduced pressure. The residue was dissolved in 300 ml ethyl acetate, then the organic solution was washed 2 times with 120 ml 1N HCl and 120 ml brine, dried over $MgSO_4$ and concentrated under reduced pressure to give 7.43 g of crude material. The crude product was purified by flash chromatography on a 330 g silica gel column (detection wave length 254 nm) with a gradient of n-hexane to n-hexane/ethyl acetate (2:1) and gave after evaporation 5.23 g (72%) HDP 30.2739 as a white solid.

MS ($ESI^+$) found: 557.17 $[MH]^+$; calc.: 557.22 ($C_{32}H_{32}N_2O_7$)

MS ($ESI^+$) found: 579.25 $[M+Na]^+$.

Example 3.4: Preparation of 6-Benzyloxy-N-Carbobenzyloxy-1-tert-butoxycarbonyl-L-tryptophan Methyl Ester HDP 30.2760

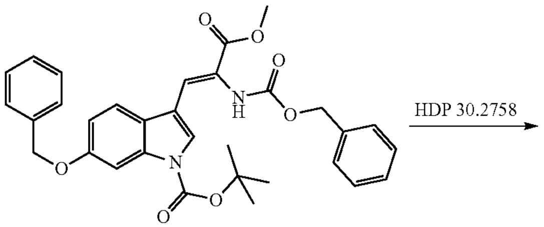

HDP 30.2739

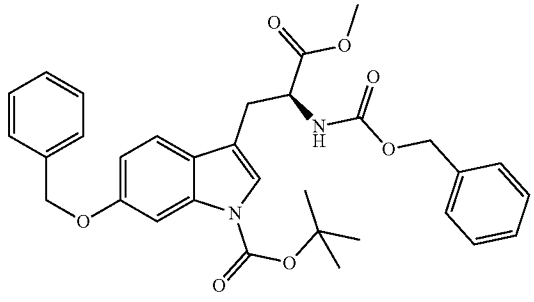

HDP 30.2760

Example 3.4.1: Synthesis of cyclooctadiene-1,5-[(R,R)-DIPAMP] Rhodium Tetrafluoroborate HDP 30.2758

The catalyst cyclooctadiene-1,5-[(R,R)-DIPAMP]rhodium tetrafluoroborate HDP 30.2758 was synthesized as described in Example 2.3.1.

Example 3.4.2: Synthesis of (S)-6-Benzyloxy-N-carbobenzyloxy-1-tert-butoxycarbonyl-tryptophan Methyl Ester HDP 30.2760

A 250 ml stainless steel autoclave was charged with 60.0 mg (0.08 mmol) cyclooctadiene-1,5-[(R,R)-DIPAMP]rhodium tetrafluoroborate HDP 30.2758 and 1000 mg (1.8 mmol) [6-Benzyloxy-1H-(1-tert-butoxycarbonyl)-3-indole]-2-(benzyloxycarbonyl-amino)acrylic acid methyl ester HDP 30.2739 in 40 ml dry methanol. After four vacuum/Ar and $H_2$ cycles, the reaction was pressurized to an initial pressure of 30 bar. The reaction was allowed to proceed for 4 days at ambient temperature. After the evaporation of the solvent, the crude product was purified by flash chromatography on a 120 g silica gel column (detection wave length 254 nm) with a gradient of n-hexane to n-hexane/ethyl acetate (2:1) and gave after evaporation 0.85 g (86%) HDP 30.2760 as a white solid.

MS ($ESI^+$) calc.: 558.23 ($C_{33}H_{34}N_2O_7$)

MS ($ESI^+$) found: 581.17 $[M+Na]^+$; 1138.83 $[2M+Na]^+$.

Example 3.5: Preparation of 6-Benzyloxy-N-carbobenzyloxy-L-tryptophan Methylester HDP 30.2790

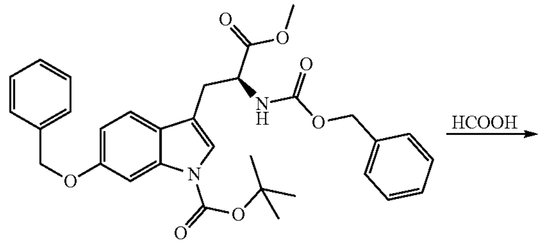

HDP 30.2760

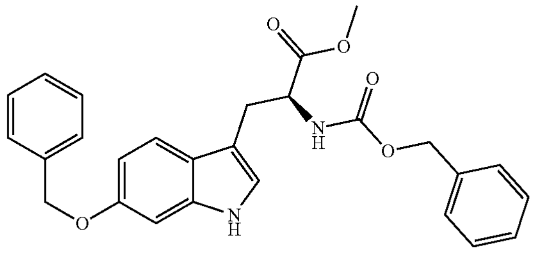

HDP 30.2790

100.0 mg (O. 18 mmol) (S)-6-Benzyloxy-N-carbobenzyloxy-1-tert-butoxycarbonyl-tryptophan methyl ester HDP 30.2760 was dissolved in 5.0 ml formic acid and stirred 1 hour at 40° C. The reaction mixture was evaporated to dryness and the residue dissolved in ethyl acetate. The ethyl acetate solution was washed with water, saturated $NaHCO_3$ and brine and dried over $MgSO_4$. After the evaporation of the solvent, the crude product was purified by flash chromatography on a 24 g silica gel column (detection wave length 254 nm) with a gradient of n-hexane to n-hexane/ethyl acetate (1:1) and gave after evaporation 29 mg (35%) HDP 30.2790 as a white solid.

MS ($ESI^+$) calc.: 458.52 ($C_{27}H_{26}N_2O_5$)

MS ($ESI^+$) found: 459.25 $[M+H]^+$.

Example 3.6: Preparation of (S)-6-Benzyloxy-N-Carbobenzyloxy-tryptophan HDP 30.2782

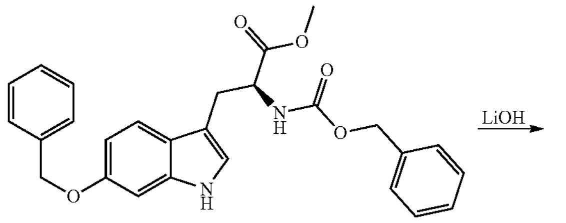

HDP 30.2790

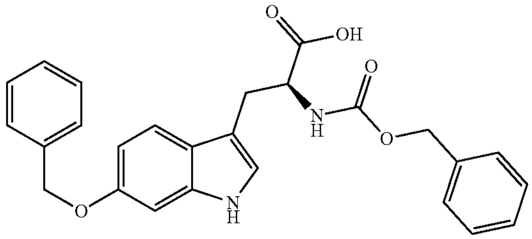

HDP 30.2782

A 2N aqueous solution of LiOH (84.7 μl) was added to a solution of HDP 30.2790 25.9 mg (0.056 mmol) in 1000 μl tetrahydrofuran/water (10:1) at ambient temperature. The reaction mixture was stirred for 2.5 hours and partitioned between ethyl acetate and 5% citric acid. The aqueous layer was extracted with ethyl acetate and the organic layers were combined, dried ($MgSO_4$) and concentrated. The resulting carboxylic acid HDP 30.2782 was purified on silica gel using dichloromethane/methanol (+1% acetic acid) as mobile phase. 13.7 mg (55%) white solid.

MS ($ESI^+$) calc.: 444.17.23 ($C_{26}H_{24}N_2O_5$)

MS ($ESI^+$) found: 445.25 $[M+H]^+$; 467.17 $[M+Na]^+$.

Example 3.7: Preparation of (S)-6-Hydroxy-N-(tert-butoxycarbonyl)-tryptophan HDP 30.2832

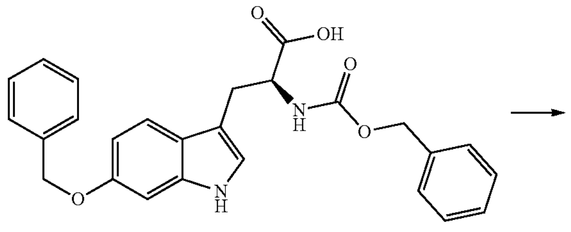

HDP 30.2782

-continued

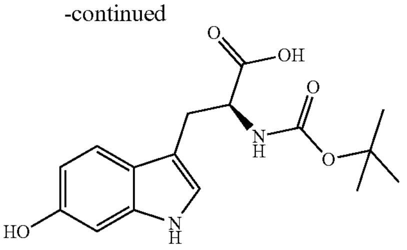

HDP 30.2832

Palladium on charcoal 10 mg (10% weight) was added to a solution of 50 mg (0.11 mmol) HDP 30.2782 in 800 μl methanol. The reaction mixture was purged three times with hydrogen and stirred for 2.5 h at room temperature. The suspension was filtered through a plug of Celite® washed with methanol and concentrated to dryness. The solid residue (22.2 mg) (S)-6-hydroxytryptophan was dissolved in 1000 μl 1,4-dioxane/water (1:1) and treated with 101 μl (0.101 mmol) 1N NaOH and 21.57 μl (0.10 mmol) Di-tert-butyl dicarbonate. The reaction mixture was stirred for 16 hours and adjusted to pH 2 with 1N hydrochloric acid. The aqueous solution was extracted three times with ethyl acetate and the combined organic phases washed with brine, dried and evaporated to dryness. The crude HDP 30.2832 was purified on silica gel using dichloromethane/methanol (+1% acetic acid) as mobile phase. 9.9 mg (31%) of a white solid. The material was identical with a reference sample.

MS ($ES^-$) calc.: 320.14 ($C_{16}H_{20}N_2O_5$)

MS ($ESI^+$) found:319.08 $[M-H]^-$.

Example 4: Preparation of cis,trans-1-(tert-butoxy-carbonyl)-2-carboxy-3a-hydroxy-6-acetoxy-1,2,3,3a,8,8a-hexahydropyrrolo[2,3-b]indole cis-HDP 30.2555 and trans HDP 30.2555 (cis,trans-6-Ac-etoxy-Hpi)

Example 4.1: Preparation of (S)-N-(tert-butoxycarbonyl)-6-acetoxy-tryptophan HDP 30.2550

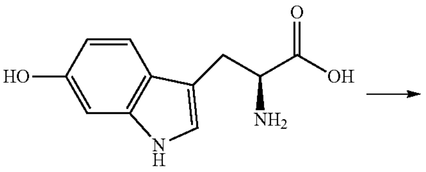

(S)-6-Hydroxy tryptophan

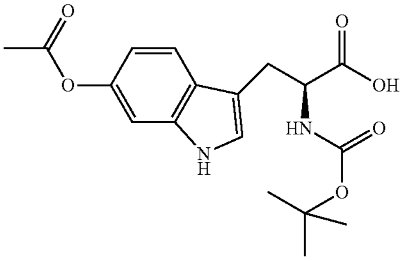

HDP 30.2550

590.0 mg (2.68 mmol) (S)-6-Hydroxytryptophan from the hydrogenation step in Example 3.7 was suspended in a mixture of 30 ml 1,4-dioxane/water 1:1 (v,v). Under argon 2.68 ml (2.68 mmol) 1N NaOH was added at once at ambient temperature. The resulting yellow solution was than treated with 574.6 ml (2.68 mmol) Boc anhydride ($Boc_2O$) and stirred for 24 hours at room temperature. The solution was acidified with 1N hydrochloric acid to pH 2.4 and extracted 3 times with 25 ml ethyl acetate. The combined ethyl acetate extracts were washed with saturated NaCl solution and dried over $MgSO_4$. Filtration and evaporation to dryness gave 785.0 mg crude material. The crude N-Boc-6-hydroxy-L-tryptophan was dissolved in 4.91 ml (4.91 mmol) 1N NaOH and treated with 463.2 ml (500.3 mg, 4.90 mmol) acetanhydride. The reaction mixture was stirred for 3 hours under argon and acidified with 5% citric acid. The aqueous phase was extracted three times with 25 ml ethyl acetate, washed with saturated NaCl and dried over $MgSO_4$. Filtration and evaporation gave 635 mg of a crude solid. The crude product was purified by flash chromatography on a 330 g silica gel column (detection wave length 254 nm) with a gradient of $CH_2Cl_2$+1% acetic acid to $CH_2Cl_2$/MeOH (15:1)+1% acetic acid and gave after co evaporation with toluene 564.4 mg (56% yield) of a white powder.

MS ($ESI^-$) found: 361.08$[M-H]^-$; calc.: 362.15 ($C_{18}H_{22}N_2O_6$)

Example 4.2: Preparation of cis,trans-6-Acetoxy-Hpi

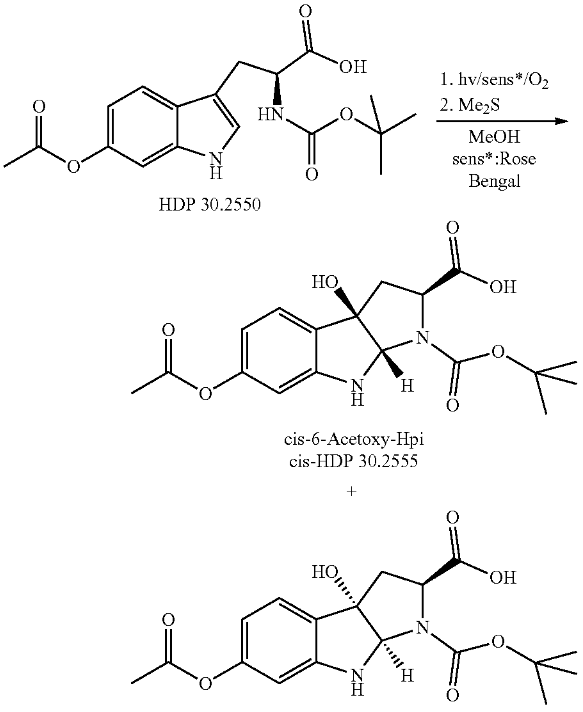

HDP 30.2550 cis-6-Acetoxy-Hpi
cis-HDP 30.2555

+ trans-6-acetoxy-Hpi
trans-HDP 30.2555

The photo-oxygenation was carried out with a 400 W high-pressure sodium vapor lamp (Sirius X400 lamp 230V, 400 W; 55000 lumen at a distance of 1.3 m). Rose Bengal is used as a dye sensitizer. The reaction was carried out in a 500 ml cylindrical reaction vessel with heat exchange jacket made of borosilicate glass, flat bottom and flat laboratory flange (DN) with two connectors with GL 18 thread. The distance from lamp to reaction vessel, was 15 cm and the reaction temperature was in a range of 3-4° C.

The final product was purified on a Teledyne ISCO Flash chromatography system with a 330 g Silica Redi Sept Flash column (Teledyne ISCO cat. 69-2203-330). Solvents $CH_2Cl_2$, —$CH_3OH$, $CH_3COOH$ were standard HPLC or BP grade. Dry oxygen (99.5% purity) was bubbled through the reaction mixture with a rate of 2-4 l per minute.

943.0 mg (2.60 mmol) N-(tert-butoxycarbonyl)-L-6-acetoxy-tryptophan HDP 30.2550 and 100 mg Rose Bengal were dissolved in 500 ml methanol and cooled to 3° C. by using a Huber cryostat with glycol/water as cooling media. The reaction solution was irradiated with the 400 W high-pressure sodium vapor lamp. During the irradiation a slow stream of oxygen was bubbled through the reaction solution. After 5 hours irradiation, oxygenation and cooling was stopped and the reaction media was treated with 10 ml of dimethyl sulfide. The mixture was stirred for 2 hours and evaporated to dryness by using a rotary evaporator with a water bath temperature of 35° C. The dark red residue was dried further in high vacuum to a crystalline solid of 1.20 g. The crude product was purified on a 330 g silica gel column (detection wave length 254 nm) with a gradient of $CH_2Cl_2$+5% acetic acid to $CH_2Cl_2$/MeOH (30:1)+5% acetic acid. 380 mg cis-HDP 30.2555 and 290 mg trans-HDP 30.2555 were eluted and co-evaporated with toluene. After lyophilisation in tert-butanol both isomers were obtained as off-white powders.

cis-1-(tert-butoxycarbonyl)-2-carboxy-3a-hydroxy-6-acetoxy-1,2,3,3a,8,8a-hexahydropyrrolo[2,3-b]indole (cis-HDP 30.2555)

380 mg cis-HDP 30.2555 yield: 39%

$^1$H-NMR (400 MHz, $CD_3OD$, δ=ppm)

δ=1.22, 1.44, 1.54 [s, 9H, $C(CH_3)_3$]; 2.23 (s, 3H, $OCOCH_3$); 2.46-2.63 (m, 2H, $CH_2$); 4.14-4.29 (m, 1H, 2-H); 5.35 (s, 1H, 8a-H); 6.39-6.46 (m, 2H, 7-H, 5-H); 7.20-7.24 (m, 1H, 4-H)

$^{13}$C-NMR (100 MHz, $CD_3OD$, δ=ppm)

δ=20.93, 28.45, 31.12, 42.80, 61.12, 69.44, 82.21, 85.82, 87.93, 104.97, 112.98, 124.84, 129.42, 151.51, 154.04, 155.97, 171.34, 175.79

MS ($ESI^+$) found: 378.92 $[MH]^+$; calc.: 378.14 ($C_{18}H_{22}N_2O_7$)

MS ($ESI^+$) found: 401.17 $[M+Na]^+$; calc.: 401.14 ($C_{18}H_{22}N_2NaO_7$)

UV/VIS ($CH_3OH$): $\lambda_{max}$=296 nm, 239 nm, 215 nm $\lambda_{min}$=266 nm, 227 nm trans-1-(tert-butoxycarbonyl)-2-carboxy-3a-hydroxy-6-acetoxy-1,2,3,3a,8,8a-hexahydropyrrolo[2,3-b]indole (trans-HDP 30.2555)

290 mg trans-HDP 30.2555 yield: 30%

$^1$H-NMR (400 MHz, $CD_3OD$, δ=ppm)

δ=1.22, 1.45, 1.54 [s, 9H, $C(CH_3)_3$]; 2.22 (s, 3H, $OCOCH_3$); 2.55-2.73 (m, 2H, $CH_2$); 4.51-4.57 (m, 1H, 2-H); 5.21-5.24 (s, 1H, 8a-H); 6.36-6.41 (m, 2H, 7-H, 5-H); 7.17-7.18 (m, 1H, 4-H)

$^{13}$C-NMR (100 MHz, $CD_3OD$, δ=ppm)

δ=20.95, 28.50, 31.12, 42.47, 60.97, 69.44, 82.06, 84.84, 87.54, 104.74, 112.67, 125.03, 128.70, 152.31, 154.22, 156.00, 171.23, 174.67

| | | |
|---|---|---|
| MS ($ESI^+$) | found: 379.00 $[MH]^+$; | calc.: 378.14 ($C_{18}H_{22}N_2O_7$) |
| MS ($ESI^+$) | found: 401.17 $[M + Na]^+$; | calc.: 401.14 ($C_{18}H_{22}N_2NaO_7$) |
| MS ($ESI^+$) | found: 779.00 $[2M + Na]^+$; | calc.: 779.28 ($C_{36}H_{44}N_4Na_2O_{14}$) |

UV/VIS ($CH_3OH$): $\lambda_{max}$=299 nm, 241 nm, 215 nm $\lambda_{min}$=268 nm, 228 nm

Example 4.3: Introduction of cis,trans-6-Acetoxy-Hpi into Amanitin Precursor Synthesis of amanitin using cis,trans-6-Acetoxy-Hpi was performed as described in PCT/EP2018/071268, the content of which is incorporated by reference hereby, mainly for purposes of enablement.

REFERENCES

Muraoka S, and Shinozawa T., J Biosci Bioeng. 2000; 89(1):73-6

Wieland T., Faulstich H. 1978. CRC Crit Rev Biochem. Vol. 5: 185-260.

Zanotti G, Mahringer C, and Wieland T., lnt J Pept Protein Res. 1987 October; 30(4):450-9;

Zanotti G, Wieland T, Benedetti E, Di Blasio 8, Pavone V, and Pedone C., lnt J Pept Protein Res. 1989 September; 34(3):222-8

Zhang P, et al., FEMS Microbiol Lett. 2005 Nov. 15; 252(2):223-8. Epub 2005 Sep. 15

What is claimed is:

1. A method for synthesizing(S)-6-acetyloxy-N-tert-butoxycarbonyl-tryptophan(HDP 30.2550) or(S)-6-hydroxytryptophan, said method comprising:

enantiomer-selectively hydrogenating of an olefinic precursor compound in the presence of at least one chiral catalyst, wherein said method comprises at least the following steps:

2. The method according to claim 1, wherein said chiral catalyst is a compound selected from the group consisting of compound

HDP 30.2758

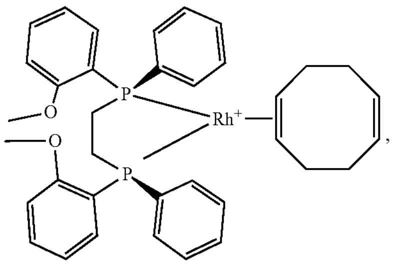

HDP 30.2758
$C_{36}H_{40}BF_4O_2P_2Rh$ (R,R)-Et-DUPHOS ($BF_{4-}$)

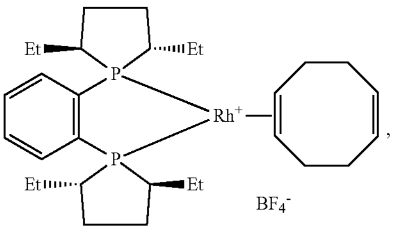

(R,R)-Et-DUPHOS ($BF_4^-$)
$C_{30}H_{48}BF_4P_2Rh$

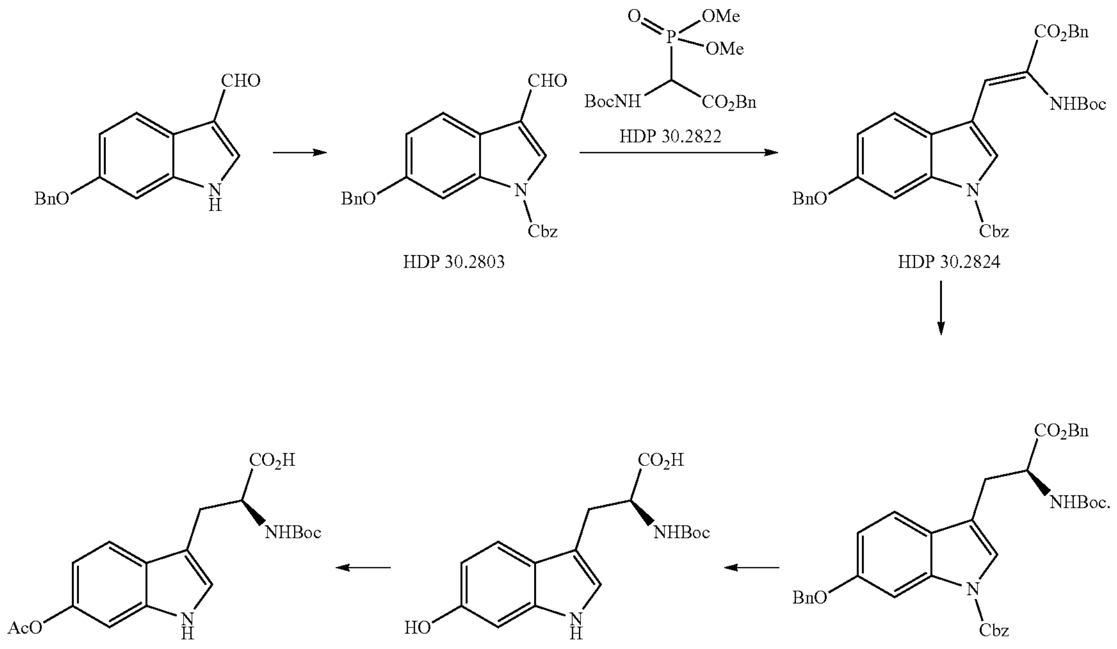

HDP 30.2803

HDP 30.2824

HDP 30.2550

HDP 30.2832

HDP 30.2826

(R,R)-DuPhos-Ferrocene ($BF_{4-}$)

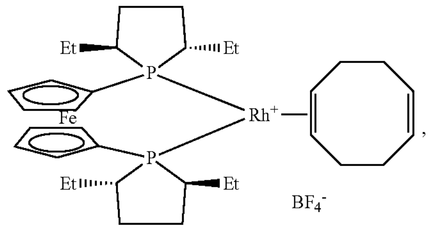

(R,R)-Et-DUPHOS-Ferrocene ($BF_4^-$)
$C_{34}H_{52}BF_4FeP_2Rh$ (R,R)-DuPhos-Ferrocene-$Et_2$($BF_{4-}$)

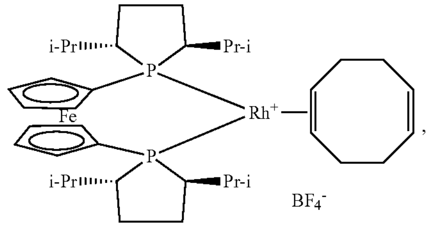

(R,R)-Et-DUPHOS-Ferrocene-$Et_2$ ($BF_4^-$)
$C_{38}H_{60}BF_4FeP_2Rh$ (R,R)-DuPhos-Alkyl($CF_3SO_{3-}$)

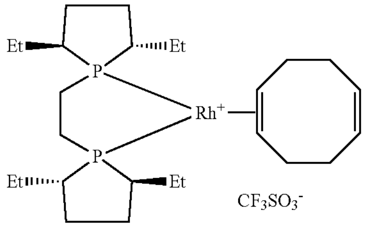

(R,R)-DUPHOS-Alkyl($CF_3SO_{3-}$)
and $C_{27}H_{48}F_3O_3P_2RhS$.

3. The method according to claim 2, wherein said chiral catalyst is compound HDP 30.2758 or (R,R)-Et-DUPHOS ($BF_{4-}$).

4. A method for synthesizing(S)-6-acetyloxy-N-tert-butoxycarbonyl-tryptophan (HDP 30.2550) or(S)-6-hydroxytryptophan, said method comprising:

enantiomer-selectively hydrogenating of an olefinic precursor compound in the presence of at least one chiral catalyst;

wherein said olefinic precursor is compound HDP 30.2824:

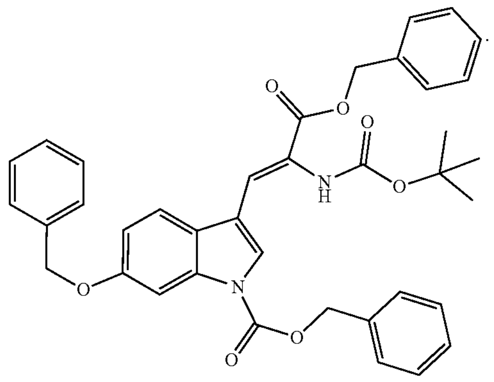

HDP 30.2824

5. The method according to claim 4, wherein said chiral catalyst is a compound selected from the group consisting of compound (R,R)-Et-DUPHOS($BF_{4-}$)

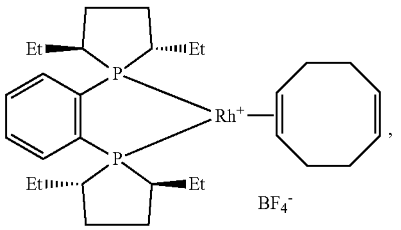

(R,R)-Et-DUPHOS ($BF_4^-$)
$C_{30}H_{48}BF_4P_2Rh$ (R,R)-DuPhos-Ferrocene($BF_{4-}$)

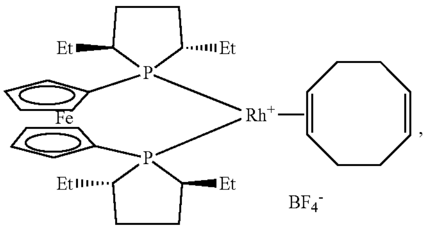

(R,R)-Et-DUPHOS-Ferrocene ($BF_4^-$)
$C_{34}H_{52}BF_4FeP_2Rh$ (R,R)-DuPhos-Ferrocene-$Et_2(BF_{4-})$

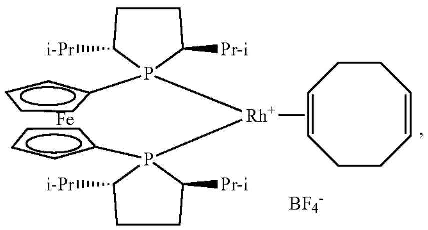

(R,R)-Et-DUPHOS-Ferrocene-$Et_2$ ($BF_4^-$)
$C_{38}H_{60}BF_4FeP_2Rh$ (R,R)-DuPhos-Alkyl($CF_3SO_{3-}$)

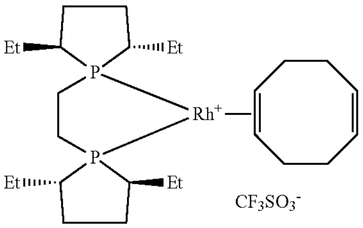

, and (R,R)-DUPHOS-Alkyl ($CF_3SO_3^-$)
$C_{27}H_{48}F_3O_3P_2RhS$ and cyclooctadiene-1,5-[(R,R)-DIPAMP] rhodium tetrafluoroborate(catalyst HDP 30.2758)

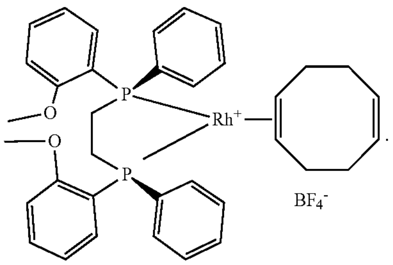

HDP 30.2758

6. The method according to claim 5, wherein said chiral catalyst is compound HDP 30.2758 or (R,R)-Et-DUPHOS ($BF_{4-}$).

7. The method according to claim 4, wherein said olefinic precursor HDP 30.2824 is synthesized by use of compound HDP 30.2822 as follows:

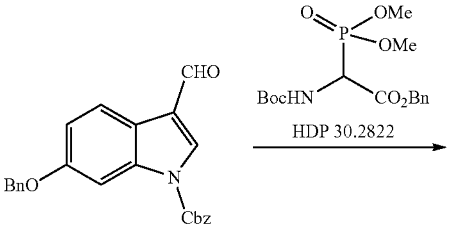

HDP 30.2803

-continued

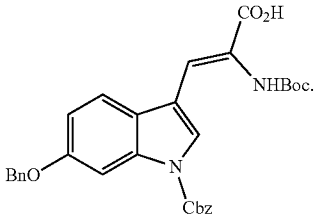

HDP 30.2824

8. The method according to claim 7, wherein said olefinic precursor is further synthesized by use of compound B:

Compound B

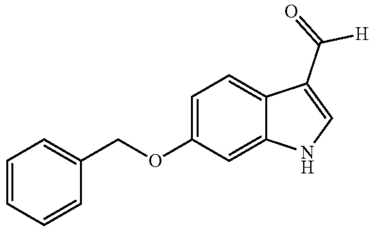

using the following reactions:

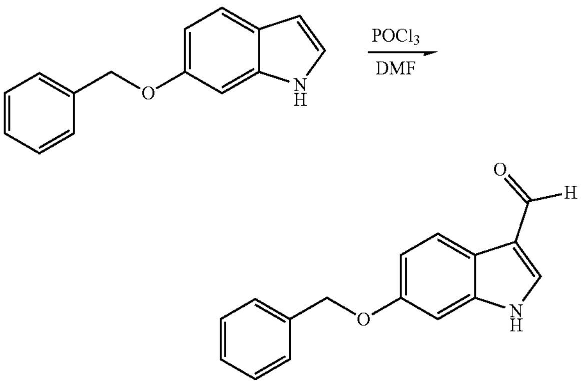

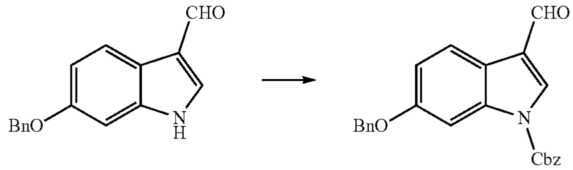

HDP 30.2803

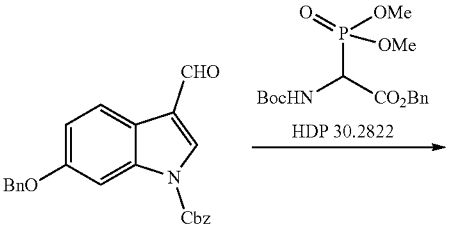

HDP 30.2803

-continued

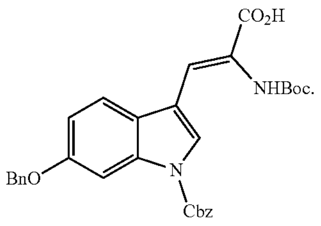

HDP 30.2824

-continued

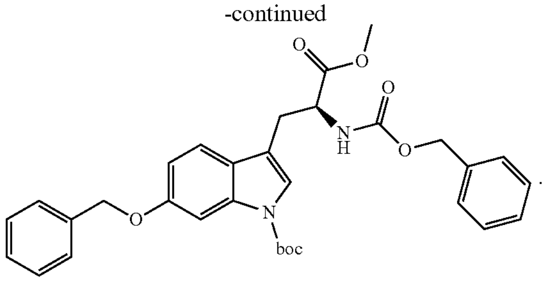

HDP30.2760

9. The method according to claim 4, wherein said method comprises the use of at least one starting or intermediate compound selected from the group consisting of

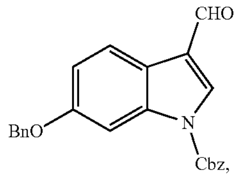

HDP 30.2803

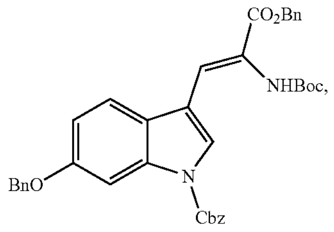

HDP 30.2824

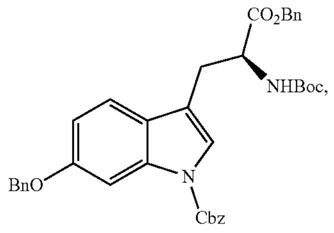

HDP 30.2826

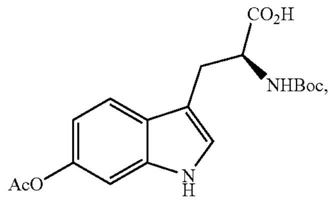

HDP 30.2550

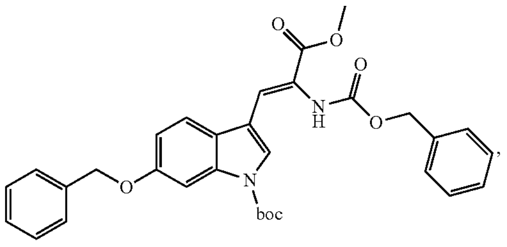

, and

HDP30.2739

10. The method according to claim 1, wherein(S)-6-acetyloxy-N-tert-butoxycarbonyl-tryptophan (HDP 30.2550) is synthesized.

11. The method according to claim 1, wherein(S)-6-hydroxytryptophan is synthesized.

12. The method according to claim 4, wherein(S)-6-acetyloxy-N-tert-butoxycarbonyl-tryptophan (HDP 30.2550) is synthesized.

13. The method according to claim 4, wherein(S)-6-hydroxytryptophan is synthesized.

14. The method according to claim 1, wherein the Boc protecting group (t-butyloxycarbonyl) and the Ac protecting group (acetyl) are removed from(S)-6-acetyloxy-N-tert-butoxycarbonyl-tryptophan(HDP 30.2550) to obtain(S)-6-hydroxytryptophan.

15. The method according to claim 4, wherein said compound HDP 30.2824 is further reacted as follows to obtain said (S)6-acetyloxy-N-tert-butoxycarbonyl-tryptophan (HDP 30.2550):

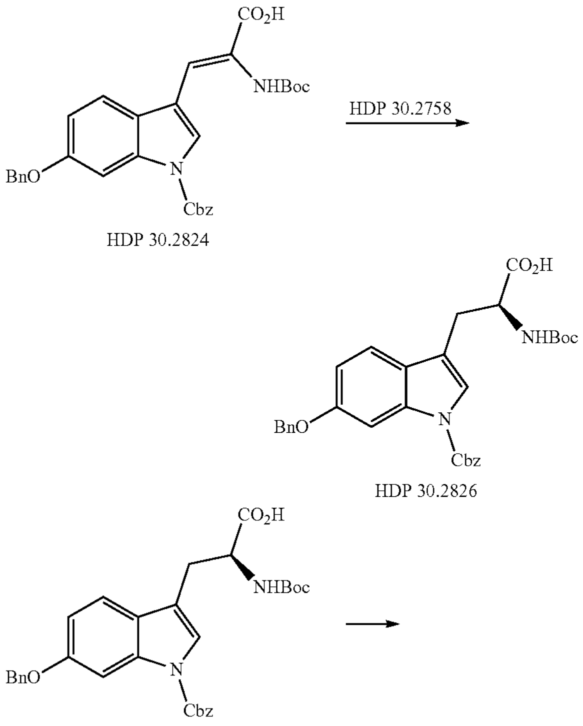

HDP 30.2824

HDP 30.2826

HDP 30.2826

-continued
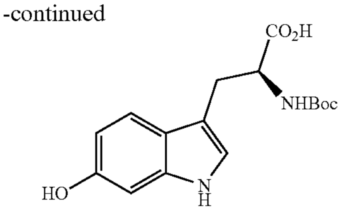
HDP 30.2832
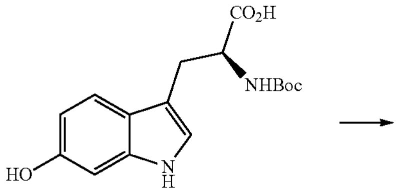
HDP 30.2832
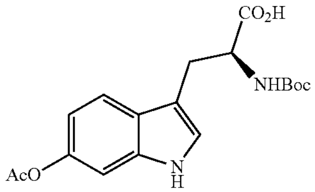
HDP 30.2550
wherein said compound HDP 30.2758 is as follows
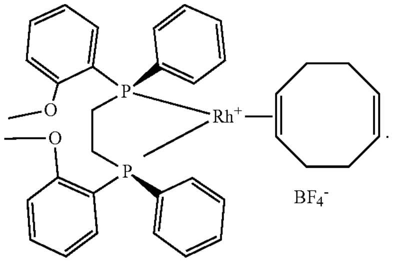
HDP 30.2758
16. The method according to claim 4, wherein the Boc protecting group (t-butyloxycarbonyl) and the Ac protecting group (acetyl) are removed from (S)6-acetyloxy-N-tert-butoxycarbonyl-tryptophan (HDP 30.2550) to obtain (S)-6-hydroxytryptophan.
* * * * *